(12) United States Patent
Deliwala

(10) Patent No.: US 11,191,469 B2
(45) Date of Patent: Dec. 7, 2021

(54) BIOPOTENTIAL MEASUREMENT SYSTEM AND APPARATUS

(71) Applicant: Analog Devices, Inc., Norwood, MA (US)

(72) Inventor: Shrenik Deliwala, Andover, MA (US)

(73) Assignee: ANALOG DEVICES, INC., Wilmington, MA (US)

( * ) Notice: Subject to any disclaimer, the term of this patent is extended or adjusted under 35 U.S.C. 154(b) by 122 days.

(21) Appl. No.: 15/988,378

(22) Filed: May 24, 2018

(65) Prior Publication Data

US 2018/0338696 A1    Nov. 29, 2018

Related U.S. Application Data

(60) Provisional application No. 62/511,709, filed on May 26, 2017.

(51) Int. Cl.

| A61B 5/0408 | (2006.01) |
|---|---|
| H03F 3/00 | (2006.01) |
| H03F 1/10 | (2006.01) |
| A61B 5/00 | (2006.01) |
| A61B 5/25 | (2021.01) |
| H03F 1/26 | (2006.01) |
| H03F 3/45 | (2006.01) |

(Continued)

(52) U.S. Cl.
CPC ............ *A61B 5/25* (2021.01); *A61B 5/6801* (2013.01); *H03F 1/10* (2013.01); *H03F 1/26* (2013.01); *H03F 3/005* (2013.01); *H03F 3/087* (2013.01); *H03F 3/45475* (2013.01); A61B 5/053 (2013.01); A61B 5/369 (2021.01); A61B 5/389 (2021.01); A61B 5/6823 (2013.01); A61B 5/7203 (2013.01); A61B 2562/0209 (2013.01); H03F 2200/261 (2013.01); H03F 2203/45551 (2013.01)

(58) Field of Classification Search
CPC .......... H03F 1/26; H03F 1/10; H03F 3/45475; H03F 3/005; H03F 2203/45551; A61B 5/0408; A61B 5/7203; A61B 2562/0209
See application file for complete search history.

(56) References Cited

U.S. PATENT DOCUMENTS

| 4,726,379 A | 2/1988 | Altman et al. |
|---|---|---|
| 6,377,845 B1 * | 4/2002 | Kinast ..................... A61B 5/30 600/547 |

(Continued)

OTHER PUBLICATIONS

International Search Report and Written Opinion issued in International Patent Application Serial No. PCT/US2018/03315 dated Sep. 13, 2018, 11 pages.

(Continued)

*Primary Examiner* — Gary Jackson
*Assistant Examiner* — Zahed Kabir
(74) *Attorney, Agent, or Firm* — Patent Capital Group

(57) ABSTRACT

System and apparatus for measuring biopotential and implementation thereof. A device for mitigating electromagnetic interference (EMI) thereby increasing signal-to-noise ratio is disclosed. Specifically, the present disclosure relates to an elegant, novel circuit for measuring a plurality of biopotentials in useful in a variety of medical applications. This allows for robust, portable, low-power, higher S/N devices which have historically required a much bigger footprint.

20 Claims, 15 Drawing Sheets

(51) Int. Cl.
*H03F 3/08* (2006.01)
*A61B 5/053* (2021.01)
*A61B 5/369* (2021.01)
*A61B 5/389* (2021.01)

(56) References Cited

U.S. PATENT DOCUMENTS

| | | | |
|---|---|---|---|
| 2003/0073916 A1* | 4/2003 | Yonce | A61B 5/30 600/509 |
| 2005/0075672 A1 | 4/2005 | Rottenberg | |
| 2008/0146894 A1* | 6/2008 | Bulkes | A61B 5/30 600/300 |
| 2008/0161883 A1* | 7/2008 | Conor | A61N 1/0456 607/48 |
| 2008/0183098 A1 | 7/2008 | Denison et al. | |
| 2008/0275316 A1 | 11/2008 | Fink et al. | |
| 2010/0327887 A1* | 12/2010 | Denison | A61B 5/0002 324/692 |
| 2011/0245702 A1* | 10/2011 | Clark | A61B 5/04284 600/523 |
| 2011/0251817 A1* | 10/2011 | Burns | A61B 5/0531 702/104 |
| 2011/0319777 A1 | 12/2011 | Mehrotra et al. | |
| 2014/0275852 A1 | 9/2014 | Hong et al. | |
| 2014/0343392 A1* | 11/2014 | Yang | A61B 5/04011 600/393 |
| 2015/0148641 A1 | 5/2015 | Morun et al. | |
| 2017/0105633 A1 | 4/2017 | Shin | |

OTHER PUBLICATIONS

Jongpal Kim et al: "Reconfigurable Multiparameter Biosignal Acquisition SoC for Low Power Wearable Platform", SENSORS, vol. 16, No. 12, Nov. 25, 2016 (Nov. 25, 2016), p. 2002, XP055730957, DOI: 10.3390/s16122002.

David Prutchi et al: "Biopotential Amplifiers" In: "Design and Development of Medical Electronic Instrumentation", Oct. 15, 2004 (Oct. 15, 2004), John Wiley & Sons, Inc., Hoboken, NJ, USA, XP055036136, ISBN: 978-0-47-.

Christian C Enz et al: "Circuit Techniques for Reducing the Effects of Op-Amp Imperfections: Autozeroing, Correlated Double Sampling, and Chopper Stabilization", Proceedings of the IEEE., vol. 84, No. 11, Sep. 1, 1996 (Sep. 1, 1996), XP055386680, US ISSN: 0018-9219, DOI: 10.1109/5.542410.

P.M. Van Peteghem et al: "Micropower high-performance SC building block for integrated low-level signal processing", IEEE Journal of Solid-State Circuits, vol. 20, No. 4, Aug. 1, 1985 (Aug. 1, 1985), XP055730607, USA ISSN: 0018-9200, DOI: 10.1109/JSSC.1985.1052397.

* cited by examiner

BIOPOTENTIAL MEASUREMENT SYSTEM AND APPARATUS

CROSS-REFERENCE TO RELATED APPLICATION

This patent application receives benefit from and/or claim priority to U.S. Provisional Patent Application Ser. No. 62/511,709, filed May 26, 2017, entitled "MEASURING BIO-POTENTIALS". This U.S. Provisional Patent application is incorporated by reference in its entirety.

FIELD OF THE DISCLOSURE

The present disclosure relates to medical equipment. More specifically, this disclosure describes apparatuses and systems for measuring biopotential while mitigating electromagnetic interference (EMI) in a patient.

BACKGROUND

Biopotential measurement is can be used in modern medical procedures. For example, biopotentials can be used for electrocardiogram (ECG), electroencephalogram (EEG), electromyography (EMG), etc.

ECG lead systems are used to obtain biopotential signals containing information indicative of the electrical activity associated with the heart and pulmonary system. To obtain biopotential signals, ECG electrodes are applied to the skin of a patient in various locations and coupled to an ECG device, e.g., an "ECG monitor" or "ECG telemetry." Placement of the electrodes is dependent on the information sought by the clinician.

The placement of the ECG electrodes on the patient has been established by medical protocols. The most common protocols require the placement of the electrodes in a three-lead, a five-lead, or a twelve-lead configuration. A three-lead configuration requires the placement of three electrodes; one electrode adjacent each clavicle bone (RA, LA) on the upper chest and a third electrode adjacent the patient's lower left abdomen (LL). A five-lead configuration requires the placement of the three electrodes in the three-lead configuration with the addition of a fourth electrode adjacent the sternum (Va) and a fifth electrode on the patient's lower right abdomen (RL). A twelve-lead configuration requires the placement of ten electrodes on the patient's body.

Four electrodes, which represent the patient's limbs, include the left arm electrode (LA lead), the right arm electrode (RA lead), the left leg electrode (LL lead), and the right leg electrode (RL lead). Six chest electrodes (V1-V6 leads) are placed on the patient's chest at various locations near the heart. Three standard limb leads are constructed from measurements between the right arm and left arm (Lead I), the right arm and the left leg (Lead II) and the left arm to left leg (Lead III). Other conventional lead configurations include a 14 leads system that incorporated additional leads located on a back surface.

An ECG lead set typically includes an array of three, five, or twelve leads as determined by the intended clinical protocol. Each individual lead wire includes, at a patient end thereof (e.g., distal end), an ECG lead wire connector configured to operably couple the lead wire to an electrode pad affixed to the body of a patient. At the opposite (e.g., proximal) end, the individual lead wires are gathered into a common coupler that is configured to operably couple the array of lead wires to an ECG device.

Leads sets are typically provided with a generous length of lead wire sufficient to reach from the patient to the ECG device. In some instances, however, the lead wire may fall short, in which case a lead wire extension cable having appropriate distal and proximal couplers may be employed. In some instances, the lead wire coupler of an ECG lead set and/or ECG lead extension may be incompatible with an available ECG device, in which case an ECG adapter may be employed that facilitates operable coupling of the otherwise-incompatible physical and/or electrical characteristics of the disparate couplers.

Radio frequency interference (RFI), sometime referred to as electromagnetic interference (EMI) or electromyography (EMG), is a disturbance that affects an electrical circuit due to either electromagnetic induction or electromagnetic radiation emitted from an external source. The disturbance may interrupt, obstruct, or otherwise degrade or limit the effective performance of a circuit. Biopotential signals are generally very low-level signals, and a typical ECG device has a very high input impedance. As a result, biopotential signals may be susceptible to RFI, particularly from devices that may be in use concurrently in a clinical environment, e.g., an electrosurgical instrument, or a microwave ablation unit. RFI may be exacerbated when an ECG lead wire extension cable is used.

Many techniques have been proposed to lessen the effects of electromagnetic interference (EMI). Unfortunately, their complexity makes many of them impermissible for the vast majority of professional uses, as well as a large proportion portable which is a burgeoning field. The inventor of the present disclosure has identified these shortcomings and recognized a need for a more elegant, robust biopotential measurement system with a small footprint. That is, a biopotential measurement which is simple enough for ubiquitous use while being versatile for portable fitness devices.

This overview is intended to provide an overview of subject matter of the present patent application. It is not intended to provide an exclusive or exhaustive explanation of the invention. Further limitations and disadvantages of conventional and traditional approaches will become apparent to one of skill in the art, through comparison of such systems with some aspects of the present invention as set forth in the remainder of the present application with reference to the drawings.

SUMMARY OF THE DISCLOSURE

System and apparatus for measuring biopotential and implementation thereof. A device for mitigating electromagnetic interference (EMI) thereby increasing signal-to-noise ratio is disclosed. Specifically, the present disclosure relates to an elegant, novel circuit for measuring a plurality of biopotentials in useful in a variety of medical applications. This allows for robust, portable, low-power, higher S/N devices which have historically required a much bigger footprint.

According to one aspect, the present disclosure is an apparatus for measuring biopotential using a current detector. Specifically, the apparatus measures current rather than voltage, as in a traditional differential amplifier heretofore used as the state of the art.

According to another aspect of the disclosure, biopotential measurement device comprises a first electrode electrically connected in series to a first high resistance resistor.

According to another aspect of the disclosure, biopotential measurement device comprises a second electrode electrically connected in series to a second high resistance resistor.

According to another aspect of the disclosure, biopotential measurement device further comprises a first electrode electrically connected in series to a first high resistance resistor.

According to another aspect of the disclosure, biopotential measurement device further comprises an amplifier electrically connected to the first high resistance resistor.

According to another aspect of the disclosure, biopotential measurement device wherein the amplifier electrically connected to the second high resistance resistor.

According to another aspect of the disclosure, biopotential measurement device wherein the amplifier is electrically connected to the first high resistance resistor through a switch.

According to another aspect of the disclosure, biopotential measurement device wherein, the biopotential measurement device is configured to explicitly measure the currents flowing in an external circuit, in which the currents are restricted to a small value by a large series resistor (Rs) by design.

According to another aspect of the disclosure, biopotential measurement device further comprises a capacitor electrically connected in parallel between the resistor and the amplifier.

According to another aspect of the disclosure, biopotential measurement device wherein, the measurement is configured by average current in a given time interval by charging a capacitor via a large resistor.

According to another aspect of the disclosure, biopotential measurement device wherein, the measurement is configured for sequential read-out of multiple potential using the same amplifier.

According to yet another aspect of the disclosure, biopotential measurement device wherein, the measurement of electrode impedance is performed by measuring currents thru the same amplifier used for measuring biopotential generated currents.

The drawings show exemplary biopotential circuits and configurations. Variations of these circuits, for example, changing the positions of, adding, or removing certain elements from the circuits are not beyond the scope of the present invention. The illustrated smoke detectors, configurations, and complementary devices are intended to be complementary to the support found in the detailed description.

BRIEF DESCRIPTION OF THE DRAWINGS

For a fuller understanding of the nature and advantages of the present invention, reference is made to the following detailed description of preferred embodiments and in connection with the accompanying drawings, in which.

DETAILED DESCRIPTION

Figure 1:
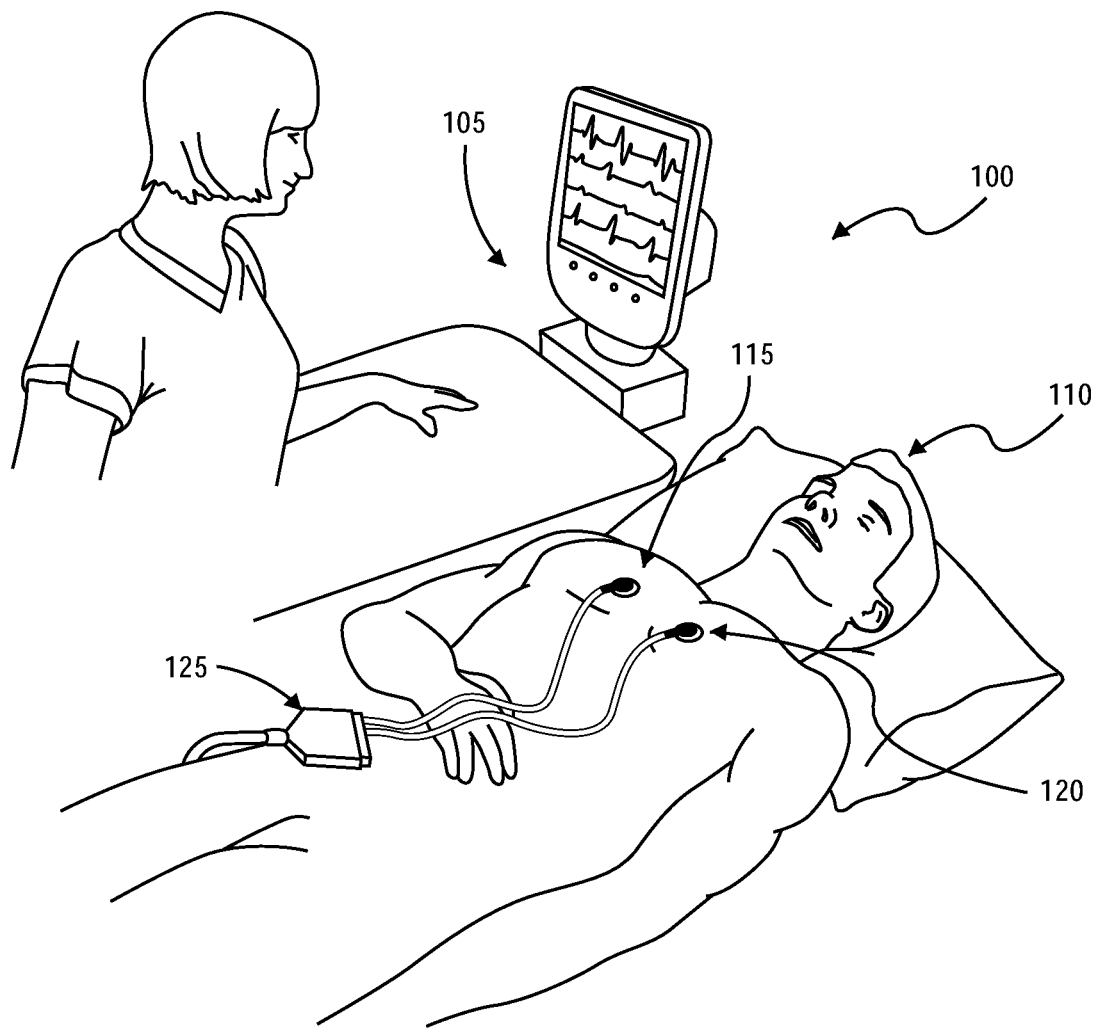
FIG. 1 shows an exemplary biopotential measurement system, in accordance with some embodiments of the disclosure provided herein.

The present disclosure relates to medical equipment. More specifically, this disclosure describes apparatuses and systems for measuring biopotential while mitigating electromagnetic interference (EMI) in a patient. And, in particular, the present disclosure relates to a biopotential measure device which isolates the measured object from the measuring apparatus and interference to provide a true differential biopotential measurement.

The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Other objects, advantages and novel features of the disclosure are set forth in the proceeding in view of the drawings where applicable.

In the field of biological electrical measurements, it has been the general practice to employ amplifying apparatus having two electrodes between which the desired potential appears and a third electrode to establish a reference point for the other two electrodes. The third electrode or ground electrode is required in order to reduce the magnitude of the common mode signals which may be introduced on the two measuring electrodes. Although three electrode amplifying devices have served the purpose, they have not proved entirely satisfactory under all conditions of service for the reasons that considerable difficulty has been experienced from the generation of interfering ground loop voltages and currents between the measured subject and the measuring apparatus.

Those concerned with the development of biopotential amplifiers have long recognized the need for isolating the measurement subject from the electrical ground of the measuring apparatus. There has been a continuous need for amplifier devices which are immune to extraneous common mode voltages and the interference of EMI and ground loop currents.

One of the most critical problems confronting designers of biopotential amplifiers has been to electrically isolate the measurement subject. In prior art measurement apparatus, the measurement subject is connected to the measuring circuit ground by a third electrode which places the subject into a position of coming in contact with another electrical system whereby extraneous currents and voltages may be developed. This present disclose contemplates solutions thereof.

The general purpose of the present disclosure is to provide a biopotential measurement system and circuit which embraces all the advantages of amplifiers employed in the state of the art which possesses none of the aforementioned disadvantages. To attain this, the present disclosure attains this through a novel current detection method, rather a voltage detection. However, the use of voltage detection amplifiers is not beyond the scope of the present invention.

Biopotential measurement is can be used in modern medical procedures. For example, biopotentials can be used for electrocardiogram (ECG), electroencephalogram (EEG), electromyography (EMG), etc.

An example of an electrical measurement circuit connected to electrodes can include a high impedance node (>>10 MΩ) that facilitates the measurement of the potential at the electrodes. These potential measurements fall in two categories: capacitive pick-up with insulated electrode with no direct current (DC) path from the electrode to the measurement circuit or a contact electrode with resistive connection. Most of the practical measurements of biopotentials are with contact electrodes.

A "lead-off" detect measurement is carried out by arranging a pull up resistors to the input and the other side connected to the ground or power supply. These resistors establish a set of potentials at the input which are "disturbed" or changed when the leads or open or there is a path for current to flow thru the body. The change in the equilibrium potential at the input are measured by comparing the case of open leads to a situation where leads are attached to the body. This will be discussed in greater detail later in the disclosure.

A high lead impedance typically resulting from use of dry electrodes makes this measurement either difficult or unreliable. This is because high impedance of the lead makes the changes in the potential at the input very small and thus hard to measure.

The impedance of the pull-up resistor acts to divide the biopotential signal as measured by the circuit. A rough estimate for the measured potential compared to the "true potential" is given by a simple formula:

$$v_m = v_{el}\left(\frac{R_{pull}}{R_{pull}+R_{el}}\right)$$

where, $v_m$ is the measured voltage, $v_{el}$ is the electrode voltage, $R_{pull}$ is the pull-up resistance and $R_{el}$ is the electrode resistance.

Considering the case for ECG which produces some of the largest signals. The peak of the ECG is ~1-2 mV. In a case where $R_{el}$~10$R_{pull}$, the measured signal will be $1/11^{th}$ the input and become very small.

The potential at the lead is a sum of two potentials: internal potentials developed by the biological function and induced potential due to induction and polarization by the external magnetic and electric fields i.e., $v_{el}=v_b+v_{ind}$. Many techniques have been suggested to separate or suppress the induced potentials. The present disclosure contemplates a novel system and apparatus which promises to be superior to the previously suggested techniques.

Generated large common mode voltages that can easily exceed few volts. Thus, the small biopotential of few mV of (or 100's of μV in case of large $R_{el}$) must be separated from presence of 3-4 orders of magnitude larger interference. Those skilled in the readily recognize the difficulty in achieving this.

In some instances, one can remove the pull-up resistors or make them very large. This makes it very difficult to make reliable measurement of whether leads are attached or not. And yet, it still does not solve the problem of large common-mode voltage at the input from the induced potentials. Any imbalance in the system—from the way electrodes are attached to differences in input impedances—can generate differential signals from the induced EMF's and now they become even more difficult to separate from the signal of interest. Much literature is devoted to filtering of measured data to separate $v_b$ from $v_{ind}$.

As discussed, this disclosure pertains to measuring biopotentials by measuring the small currents generated in the external electrical circuit rather than the potential itself. The techniques described herein are more robust in view of the external electrical interference, provides a richer data that includes impedance of the electrode/body system as well as potentials, and can consume far less power to carry out the measurement.

Turning to FIG. 1, an exemplary biopotential measurement system 100 is depicted, in accordance with some embodiments of the disclosure provided herein. Biopotential measurement system 100 comprises a biopotential computational receiver and display 105, a first lead 120, a second lead 115 and a lead junction 125. Those of ordinary skill will recognize that the simple representation of the present embodiment.

In practice, patient's 110 heart and neurological function produces a detectable voltage potential. First lead 120 and second lead 115 are disposed on opposite sides of patient's 110 heart in order to maximize detectable potential. First lead 120 and second lead 115 are fed to lead junction 125 which consequently is directed to a biopotential measurement system 100. An operator can readily read the measured results from biopotential computational receiver and display 105.

With respect to one or more described embodiments, an ECG is characterized. However, other biopotential measurements are not beyond the scope of the present invention, such as, electrocardiogram (EKG), electroencephalogram (EEG), electromyography (EMG), etc.

Figure 2:
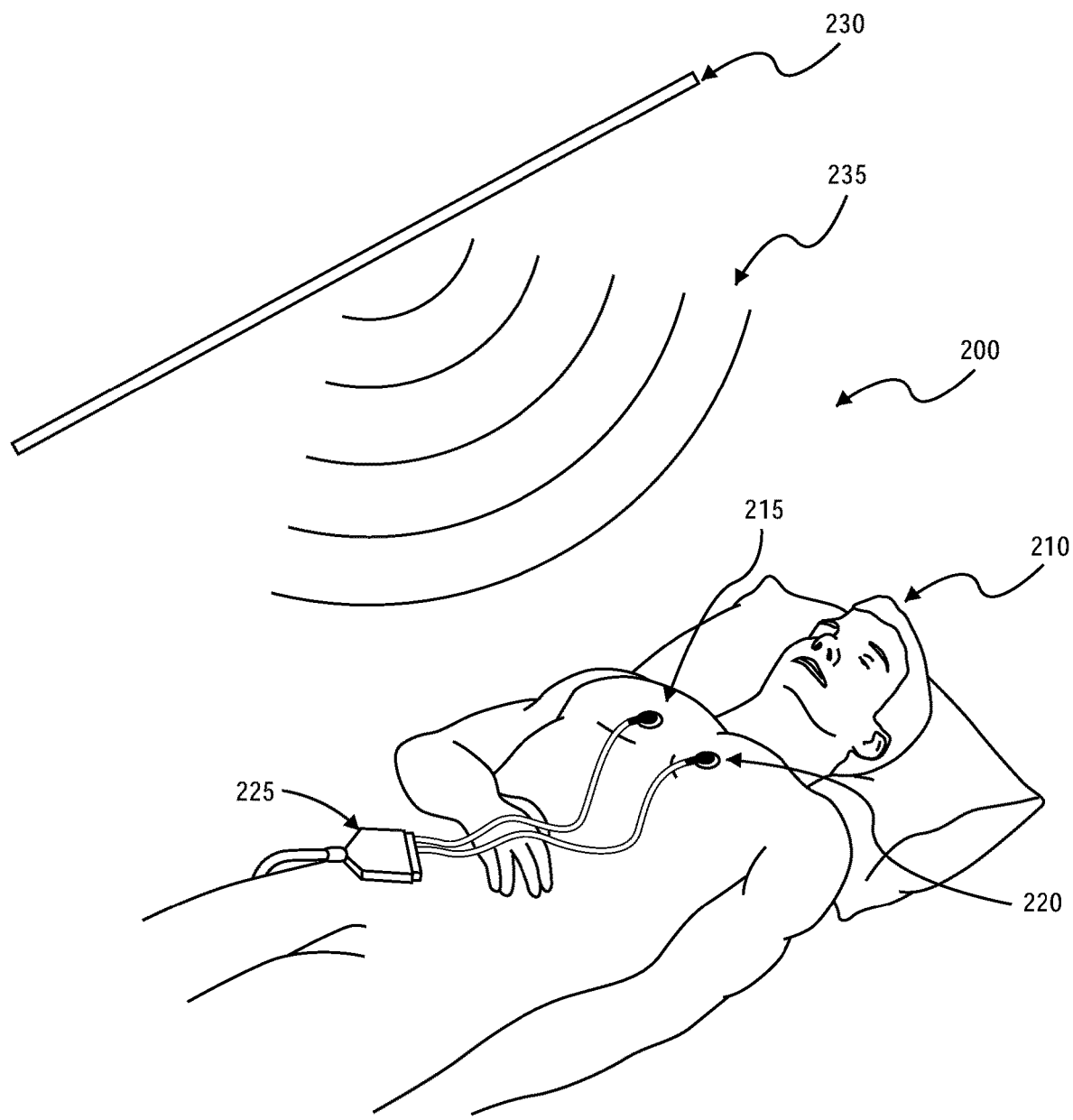
FIG. 2 shows an exemplary biopotential measurement system with a patient subjected to electromagnetic interference (EMI), in accordance with some embodiments of the disclosure provided herein.

FIG. 2 shows an exemplary biopotential measurement system with a patient 210 subjected to electromagnetic interference (EMI) 235, in accordance with some embodiments of the disclosure provided herein. Biopotential measurement system 200 comprises a biopotential computational receiver and display (not shown), a first lead 220, a second lead 215 and a lead junction 225. Those of ordinary skill will recognize that the simplified representation of the present embodiment.

Patient's 210 heart and neurological function produces a detectable voltage potential. First lead 220 and second lead 215 are disposed on opposite sides of patient's 210 heart in order to maximize detectable potential. First lead 220 and second lead 215 are fed to lead 225 which consequently is directed to a biopotential measurement system.

In practice, patience 210 is exposed to EMI 235 which is produced by any nearby electronic equipment, power lines, and even the biopotential measuring system itself. Most commonly, this comes in the form 60 cycle line frequency, which is used to carry electricity from power lines 230 to homes and institutions. The signal is pervasive. However, this interference dominates small signal measurements, such as, in the present disclosure which attempt to overcome the problem which plagues the state of the art.

Figure 3:
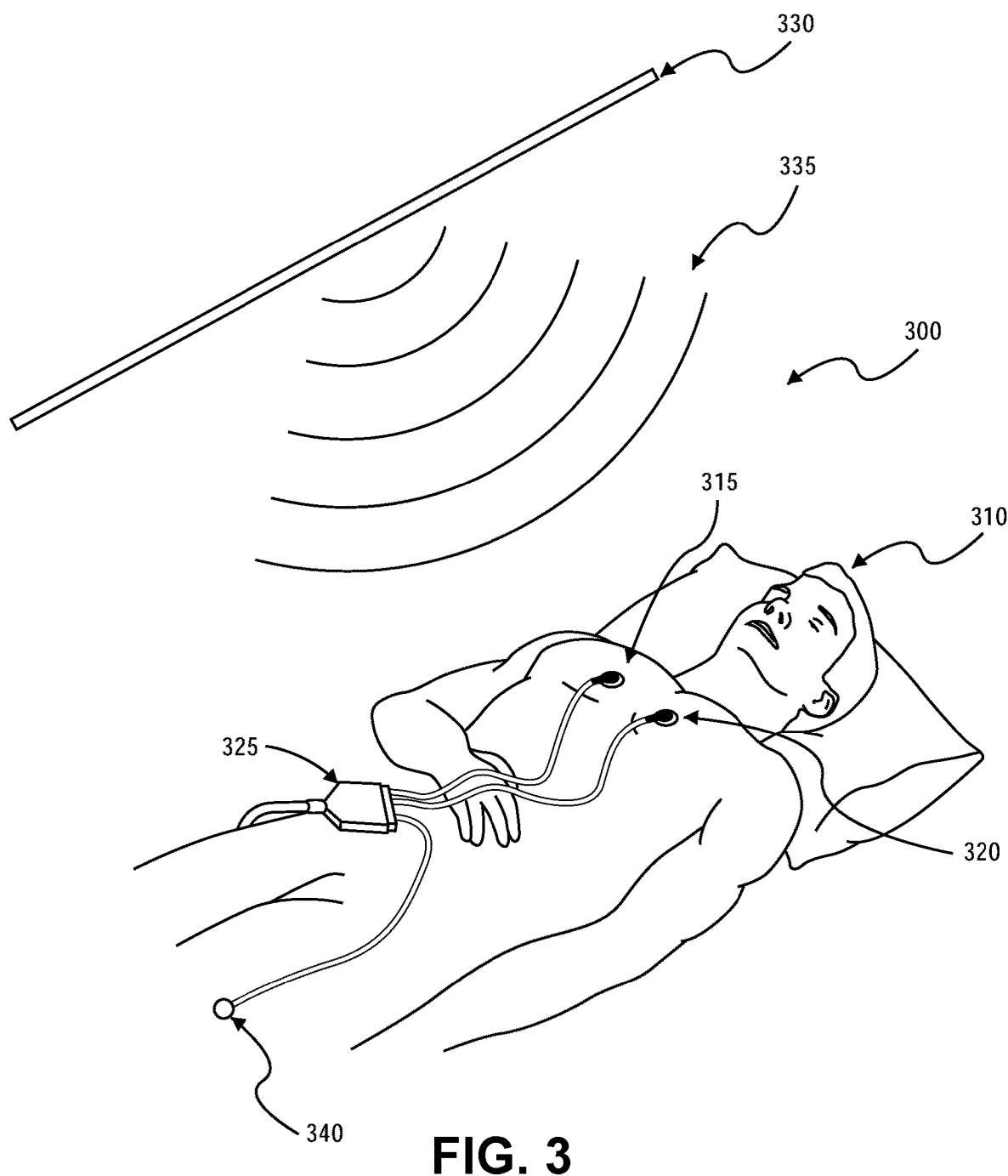
FIG. 3 shows an exemplary biopotential measurement system with a patient subjected to electromagnetic interference (EMI) with a third cancellation lead attached, in accordance with some embodiments of the disclosure provided herein.

FIG. 3 shows an exemplary biopotential measurement system 300 with a patient 310 subjected to electromagnetic interference (EMI) 335 with a third cancellation lead 340 attached thereto, in accordance with some embodiments of the disclosure provided herein. Biopotential measurement system 300 comprises a biopotential computational receiver and display (not shown), a first lead 320, a second lead 315, a third cancellation lead 340 and a lead junction 325.

As previously discussed, patience 310 is exposed to electromagnetic interference (EMI) 335 which is produced by any nearby electronic equipment, power lines 330, and even the biopotential measuring system itself, in practice. Commonly, this comes in the form 60 cycle line frequency, which is used to carry electricity from power lines 330 to homes and institutions.

In one or more embodiments, the third cancellation electrode 340 (often called the right leg drive in ECG parlance) is driven in such a way to cancel the local common mode potential as far as possible. For example, biopotential measurement system 300 can measure the electromagnetic interference (EMI) permeated patient 310 at third cancellation lead 340 and consequently add an inverted signal of the similar magnitude to achieve a cancellation.

As one in the art can appreciate, this can be problematic in a dynamic situation where the magnitude of the induced potential changes rapidly. This can happen if the person is moving around in a complex environment of external electric and magnetic fields produced by any modern office or home.

In some embodiments, the AC is coupled to the electrical measurement circuit to avoid the DC common mode which can be 10's of volts. This is substantially larger than the ability of electronic circuits operating at low supply voltages to handle. This AC coupling comes at a substantial reduction in functionality: slow settling to any sudden impulses at the input such as lotion of the leads, connect/disconnect, use of large capacitors/complex feedback circuits to set a low high pass frequency <1 Hz, distortion and delay of the signal itself to name a few. The present disclosure contemplates novel systems and apparatus to mitigate electromagnetic interference (EMI) and also retain functionality.

Figure 4:
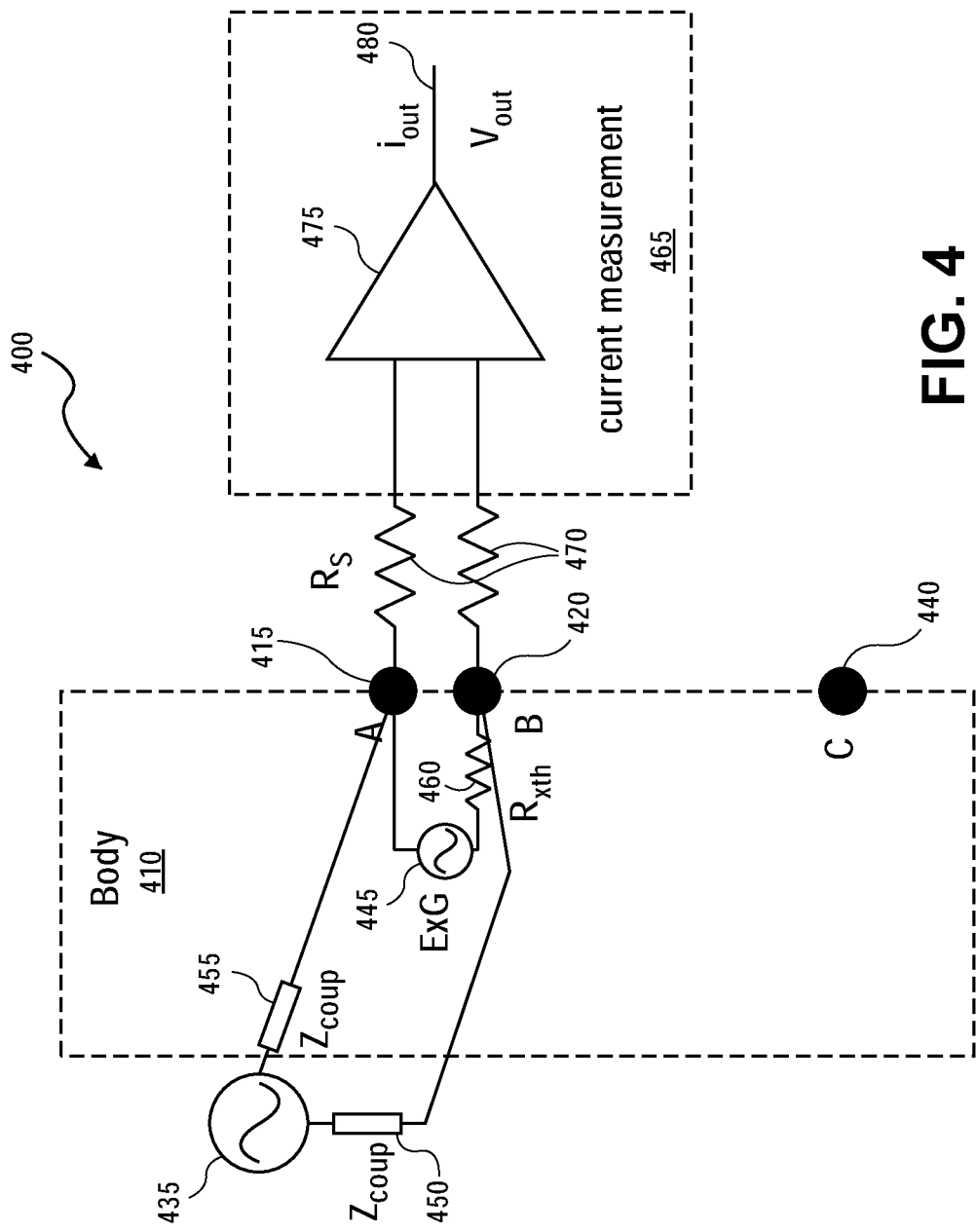
FIG. 4 is an exemplary schematic diagram of biopotential measurement circuit, in accordance with some embodiments of the disclosure provided herein.

FIG. 4 is an exemplary schematic diagram of modeled biopotential measurement system 400, in accordance with some embodiments of the disclosure provided herein. Those skilled in the art will recognize that part of biopotential measurement circuit 400 is a heuristic model of the previous embodiment depicted in FIG. 3. The parallels and applications will now be discussed in greater detail.

Biopotential measurement system 400 comprises electromagnetic interference (EMI) voltage source 435, A lead coupled complex impedance 455, B lead coupled complex impedance 450, A lead electrode 415, B lead electrode 420, C lead electrode 440, biopotential voltage source 445, biopotential Thevenin resistance 460, electrode resistances 470, and current measurement 465.

Electromagnetic interference (EMI) voltage source 435 models induced voltage on A and B lead electrodes 415, 420 from electromagnetic interference (EMI) passing through the air and body 410. Similarly, A lead coupled complex impedance 455 and B lead coupled complex impedance 450 model the complex coupled impedance from the electromagnetic interference (EMI) source and A lead electrode 415 and B lead electrode 420, passing through the ambient surrounds and body 410.

Biopotential voltage source 445 is a heuristic model of the biopotential of the heart, in one or more embodiments. Similarly, biopotential Thevenin resistance 460 is the model Thevenin resistance associated with biopotential voltage source 445. Electrode resistances 470 are resistances associated with the sticky leads placed on the body 410 which are well known in the art.

The circuits shown in FIG. 4 substantially reduces most of the difficulties mentioned in conventional measurement system above. It also improves on the convenience and robustness of the system which the more difficult to quantify. Current measurement circuit 465 comprises current amplifier and detector 475 from electrodes 470 to output 480.

In one or more embodiments, current measurement circuit 465 comprises a current amplifier. In other embodiments, current measurement circuit 465 comprises integrating amplifier so that the output is proportional to the current integrated over a fixed amount of time or proportional to the charge. For example, Analog Devices ADPD1080 is one of the many ASIC's available that performs this measurement. In yet another, embodiment, current measurement circuit 465 comprises off the shelf differential amplifier and current detector. However, any suitable current detection method, sensor, circuit or device is not beyond the scope of the present invention.

For example, any of the following can be used for current sensing and detection, according to some embodiments of the present disclosure: Hall effect IC sensor; Transformer or current clamp meter; Fluxgate Transformer Type; Resistor, whose voltage is directly proportional to the current through it; Fiber optic current sensor, using an interferometer to measure the phase change in the light produced by a magnetic field; and, Rogowski coil, electrical device for measuring alternating current (AC) or high speed current pulses. The significance of the foregoing will now be discussed in greater detail.

In practice, the electrical circuit measures the current produced by the potential at the electrodes 470 and treats the biopotential voltage source 445 as a battery with a relatively high internal resistance, biopotential Thevenin resistance 460. This current is driven into external electrical circuit which measures it. The external electrical circuit 465 provide a load to the "bio-battery" that is of the order of the internal resistance (biopotential Thevenin resistance 460) of the source (biopotential voltage source 445) that generates the biopotential.

This external load resistance can be varied for a rich insight into the nature of the source of bio-electricity. Typical values will be ~0.2-1 MΩ.

As stated, lead-off detection is an important object of the state of the art. In the present embodiment, lead-off detection natural flows and is achieved by measuring the biopotential. Put simply, the measurement current simply stops flowing into the measurement circuit 465 from electrodes.

The method allows for direct measurement of electrode resistance 470 by using the same circuit by making small perturbation in the voltage at the nodes of the electrodes. This allows complete characterization of electrode characteristics including its complex impedance. Thus, it may be used to not only detect whether leads or electrodes are connected but the quality of connection.

Large electrode resistance 470 reduces the current that flows through the measurement circuit 465. Since most biopotential measurements require ~100 Hz bandwidth (BW), it is this bandwidth (BW) and the noise of the amplifier that will set the maximum permissible electrode resistance. A rough estimate of the upper limit of the electrode resistance is the following:

$$R_{el}^{max} \sim \frac{V_{nreqd}^{bio}}{i_{nrms}} = \frac{10\ \mu V}{100\ fA} = 100\ M\Omega$$

Thus, the maximum electrode resistance that can be tolerated depends on the noise requirement on the biopotential and the noise performance of the current measuring amplifier. In the equation above, 10 μV is used for the noise requirement on the measurement of the biopotential and a reasonable current amplifier with 100 fA of root mean square (RMS) noise in 100 Hz bandwidth (BW).

This is better than or comparable to the best state of the art systems. Again, traditional state of the art systems cannot measure the "quality of electrode" or quantify its impedance.

The present embodiment depicted in FIG. 4 is considerably more immune to external electrical and magnetic fields than a potential measuring system. Advantages of the embodiments are readily apparent to those of skill in the art. Some of the advantages include the following.

The present embodiment allows the measurement of the current from the body with extremely low duty cycle for the power to the electronic circuit. For example, for 100 Hz measurement rate, there may be a passive integration of currents on the sense capacitor $C_{sense}$ over 10 ms while the charge may be measured in 10's of μs. This means that the sampling electronics can remain powered off most of the time. This may allow average current to be below 10's of μA enabling new battery powered applications.

Another advantage is the present embodiment allows for the entire system to be always "DC coupled" and easily scales to higher bandwidth. Since the induced coupling is low, a very gentle filtering is necessary to see good electrocardiogram (ECG or EKG) signals as well as other potential measurements. This reduces or eliminates distortion in the measured shape of the waveform.

Another advantage is the present embodiment allows for directly providing the "state of the electrode" by measuring impedance.

Also, the same amplifiers may be used (after providing for input matrix that allows for connection to other sensors) for other measurements of sensors that produce currents or charges in response to stimulus such as photodetectors, pyroelectric sensors, capacitors etc. This allows for high level of integration as well as synchronous measurement between different sensors, which may be important for many applications.

Instead of measuring the potential between A lead electrode 415 and B lead electrode 420, the circuit shown in FIG. 4 measures the current flowing in the measurement circuit due to internal biopotentials. The source of the biopotential—be it electrocardiogram (ECG or EKG), EEG etc.—can be a complex distributed source that is not amenable to a simple lumped element analysis. For example, this would be the case for a variable battery with a single fairly high internal resistance, which can be modelled as effective Thevenin resistance 460 of the internal battery (biopotential voltage source 445), shown as $R_{xth}$. The source may not be capable of supplying maximum current which is given:

$$i_{ExGMax} < \frac{V_{ExG}}{R_{xth}}$$

This can be due to complex interplay of local electrochemistry and equipotential lines inside the body. $R_{xth}$ may be dominated by the electrode impedance, skin impedance etc. But the source must be seen as capable of providing some current so long as the load resistance is large and these currents are small. Practical measurements on human subject's bear this out and it has been observed that roughly couple of nA of the currents will flow thru the external circuit and the electrocardiogram (ECG or EKG) signals can be measured by plotting the current waveform.

The resistance $R_s$ 470 in FIG. 4 are provided to keep the currents at low levels (in case the electrode and skin resistance goes below few 100 kΩ). This series resistance is chosen to be a few hundred kΩ to keep the total currents coming from the body to less than a few nA.

As an example, by setting $R_s$=500 kΩ, the measured currents were of the order of 0.5 nA. Since these data was taken with dry, small electrodes, it can be estimated that additional 1-2 MΩ must be in series with $R_s$ due to the electrodes. This, means that the internal voltage driving this current can be estimated and plotted on the right y-axis. It shows the correct magnitude for the electrocardiogram (ECG or EKG) signal. In the above case, each data point corresponds to the current averaged over 500 μs and the data was taken at 250 Hz. Thus, the measurement bandwidth was from DC to ~2 kHz.

Figure 5:
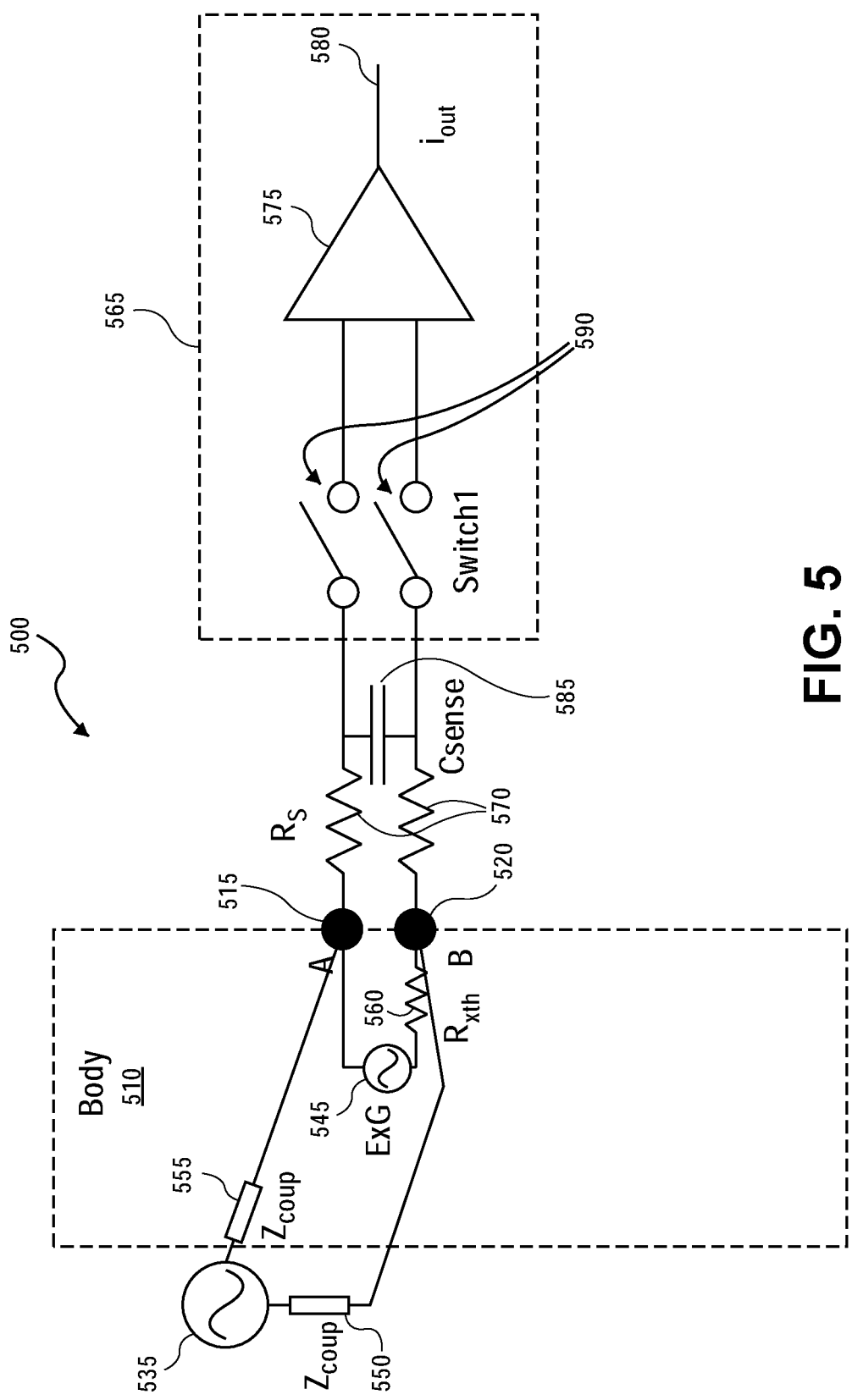
FIG. 5 is an exemplary schematic diagram of a biopotential measurement circuit that includes a switch in an open position, in accordance with some embodiments of the disclosure provided herein.

FIG. 5 is an exemplary schematic diagram of a modeled biopotential measurement system 500 that includes a switch 590 in an open position, in accordance with some embodiments of the disclosure provided herein. Again, those skilled in the art will recognize that part of biopotential measurement circuit 500 is a heuristic model.

Biopotential measurement system 500 comprises electromagnetic interference (EMI) voltage source 535, A lead coupled complex impedance 555, B lead coupled complex impedance 550, A lead electrode 515, B lead electrode 520, C lead 540, biopotential voltage source 545, biopotential Thevenin resistance 560, electrode resistances 570, sense capacitor 585, and switch(es) 590 and current measurement 565.

Electromagnetic interference (EMI) voltage source 535 models induced voltage on A and B lead electrodes 515, 520 from electromagnetic interference (EMI) passing through the air and body 510. Similarly, A lead coupled complex impedance 555 and B lead coupled complex impedance 450 model the complex coupled impedance from the electromagnetic interference (EMI) source and A lead electrode 515 and B lead electrode 520, passing through the ambient surrounds and body 510.

Biopotential voltage source 545 is a heuristic model of the biopotential of the heart, in one or more embodiments. Similarly, biopotential Thevenin resistance 560 is the model Thevenin resistance associated with biopotential voltage source 545. Electrode resistances 570 are resistances associated with the sticky leads placed on the body 510 which are well known in the art.

In the open phase where switch(es) 590 is open as shown in FIG. 5, the sense capacitor 585 is charged to the potential of the electrodes. It will take a few multiples of the time constant $\tau_{ch} \sim R_s C_{sense}$. Note that the electrode resistances $R_s$ 570 may be replaced by the effective series resistance including that of electrodes. This charge on the capacitor is then measured by the amplifier in the closed phase as shown in FIG. 6, which will now be discussed in greater detail.

Figure 6:
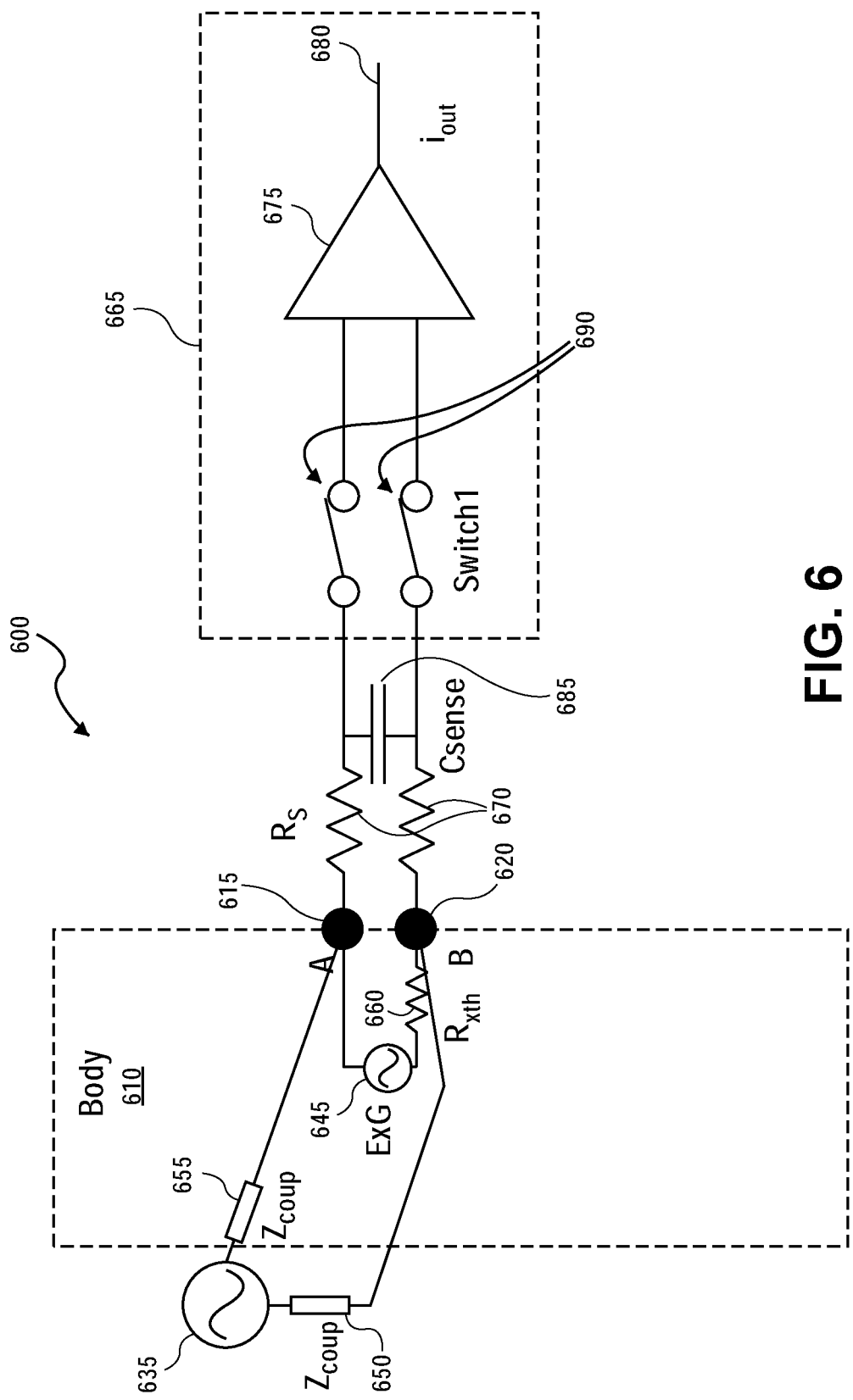
FIG. 6 is an exemplary schematic diagram of a biopotential measurement circuit that includes a switch in a closed position, in accordance with some embodiments of the disclosure provided herein.

FIG. 6 is an exemplary schematic diagram of a modeled biopotential measurement system 600 that includes a switch 690 in a closed position, in accordance with some embodiments of the disclosure provided herein. Again, those skilled in the art will recognize that part of biopotential measurement circuit 600 is a heuristic model, in one or more embodiments.

biopotential measurement system 600 comprises electromagnetic interference (EMI) voltage source 635, A lead coupled complex impedance 655, B lead coupled complex impedance 650, A lead electrode 615, B lead electrode 620, C lead 640, biopotential voltage source 645, biopotential Thevenin resistance 660, electrode resistances 670, sense capacitor 685, and switch(es) 690 and current measurement 665.

In some embodiments, electromagnetic interference (EMI) voltage source 635 models induced voltage on A and B lead electrodes 615, 620 from electromagnetic interference (EMI) passing through the air and body 610. Similarly, A lead coupled complex impedance 655 and B lead coupled complex impedance 650 model the complex coupled impedance from the electromagnetic interference (EMI) source and A lead electrode 615 and B lead electrode 620, passing through the ambient surrounds and body 610.

As stated, biopotential voltage source 645 is a heuristic model of the biopotential of the heart, in one or more embodiments. Similarly, biopotential Thevenin resistance 660 is the model Thevenin resistance associated with biopotential voltage source 645. Electrode resistances 670 are resistances associated with the sticky leads placed on the body 610 which are well known in the art.

In the present embodiment depicting a closed phase in FIG. 6, amplifier brings the sense capacitor 685 to zero (or close to zero) differential voltage and the charge on the capacitor (average of the current flowing from the body) is measured. This can be done in a very short time (order of a few μs or $\tau_m \sim R_{in} C_{sense}$) The entire process can be repeated to improve signal to noise ratio. Note that the charging time can be milliseconds and occurs passively while the measurement time can be microseconds and is the only time that substantial power needs to be dissipated by electronic circuit.

As an example, with roughly a several MΩ of effective series resistance and 100 pF for the sense capacitor 685, $\tau_{ch} \sim 100$ μs. With the charging time of ~400 μs gives adequate time for charging the capacitor. This is then discharged into a circuit with built in switches.

The fundamental reason for this very important and commercially valuable improvement is due to the fact that the external source that induces potentials in the body must drive current into the measurement system. From EM simulations and empirical observations, it is known that electric field coupling can be modelled by capacitive coupling with $C_{coupling} \sim 1-10$ pF. A 60 Hz this corresponds to $|Z| \sim 250-2500$ MΩ. Thus, this large impedance of the inducing source results in a very small currents into the amplifier.

Furthermore, the presence of much lower impedance electrodes will change the local potentials on the surface such that the actual currents driven into the measurement circuit from external electric field will be even smaller. This shows that the new measurement scheme is robust to the environmental interference.

Figure 7:
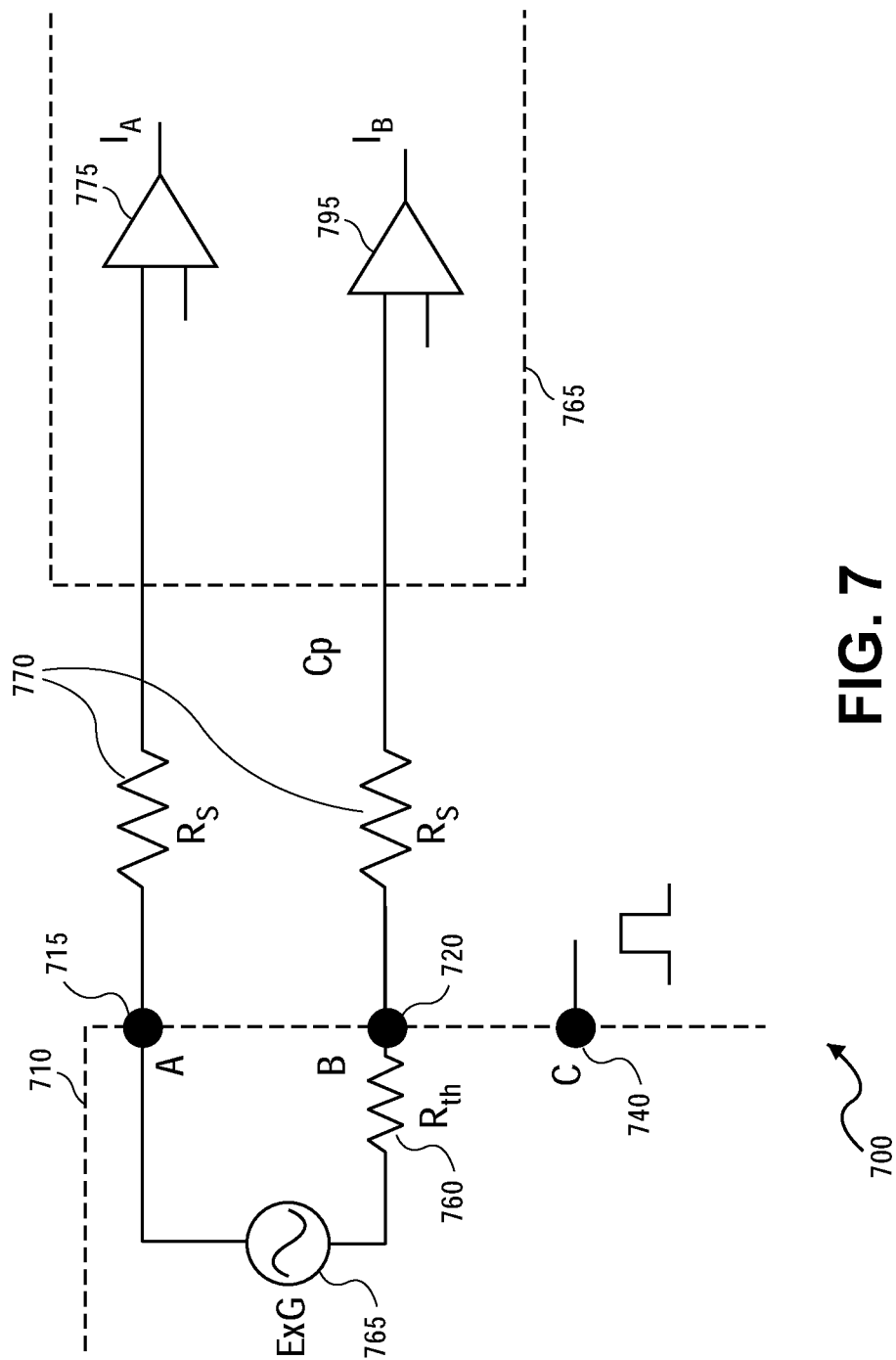
FIG. 7 is an exemplary schematic diagram of a biopotential measurement circuit illustrating the use of a third electrode, in accordance with some embodiments of the disclosure provided herein.

FIG. 7 is an exemplary schematic diagram of biopotential measurement system 700 with a third C lead electrode 740, in accordance with some embodiments of the disclosure provided herein. biopotential measurement system 700 comprises A lead electrode 715, B lead electrode 720, C lead electrode 740, biopotential voltage source 745, biopotential Thevenin resistance 760, electrode resistances 770, and current measurement 765.

In one or more embodiments, biopotential voltage source 745 is a heuristic model of the biopotential of the heart, in one or more embodiments. Similarly, biopotential Thevenin resistance 760 is the model Thevenin resistance associated with biopotential voltage source 745. Electrode resistances 770 are resistances associated with the sticky leads placed on the body 710 which are well known in the art.

In practice, FIG. 7 shows an example circuit for the measurement of the electrode impedance. In one or more embodiments biopotential measurement system 700 involves use of third electrode (C lead electrode 740) to drive a current and measure the response at the two electrodes A and B (A lead electrode 715, B lead electrode 720) independently. In this case, A lead electrode 715 and B lead electrode 720 are attached to a separate amplifiers, 775, 795 whose outputs are measured separately.

The biopotential measurement takes the difference between the output while in the impedance measurement mode, each measurement can be monitored separately. In some embodiments, this could be used in "lead-off" detection. In others, this could be used for lead coupling characterization and/or complex impedance quantification.

Figure 8:
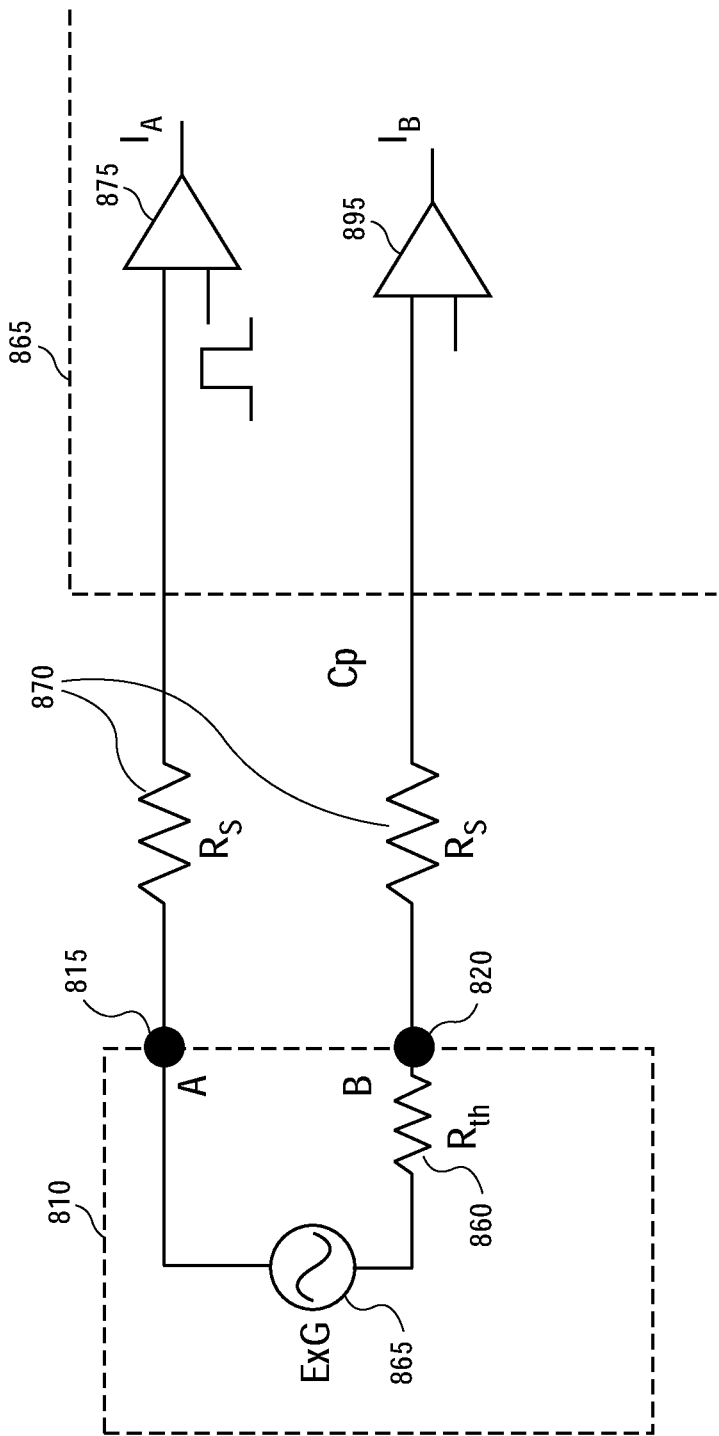
FIG. 8 is an exemplary schematic diagram of a measurement circuit comprising electrode impedance, in accordance with some embodiments of the disclosure provided herein.

FIG. 8 is an exemplary schematic diagram biopotential measurement system 800, in accordance with some embodiments of the disclosure provided herein. biopotential measurement system 800 comprises A lead electrode 815, B lead electrode 820, biopotential voltage source 845, biopotential Thevenin resistance 860, electrode resistances 870, and current measurement 865. Current measuring circuit comprises amplifiers 875, 895.

In one or more embodiments, In FIG. 8 shows an example circuit to measure the impedance without the use of third electrode. In this case, each of the amplifiers 875, 895 generate a voltage pulse at the summing node—by changing the bias point—and measuring the response. This can be carried out in multiple ways. One can simply pulse node A and measure the response at both the amplifiers. Equal currents and opposite currents will flow in both the amplifiers if the electrodes are properly connected. One can also separately pulse A and B (A lead electrode 815, B lead electrode 820) to figure out which electrode is attached to the body or if both are loose. The table below shows possible outcomes.

| | Output of Amplifier A | Output of amplifier B | Condition of electrodes |
|---|---|---|---|
| Pulse A | DC current in A | Opposite to the DC current in A | Both electrodes are attached |
| Pulse A | No DC current in A, large AC spikes at the rising and falling edges | No appreciable currents in B | B is most likely detached, A is attached to the body due to large capacitive coupling. |
| Pulse B | No appreciable currents in A | No DC current in B, small but definite AC spikes at the rising and falling edges | |

Essentially, the response to the voltage step directly measures the impedance quantitatively. Thus, the disclosed measurement technique is directly and inherently compatible with impedance measurement of the electrodes and thus provides a natural method for positive lead-off detection. Note that lack of any currents in the circuit will directly measure the fact that there are no sources connected to the electrodes but it may not be sufficient as induced voltages on non-attached electrodes may induce currents into each circuit but they cannot induce circular DC current unless both electrodes are attached.

Figure 9:
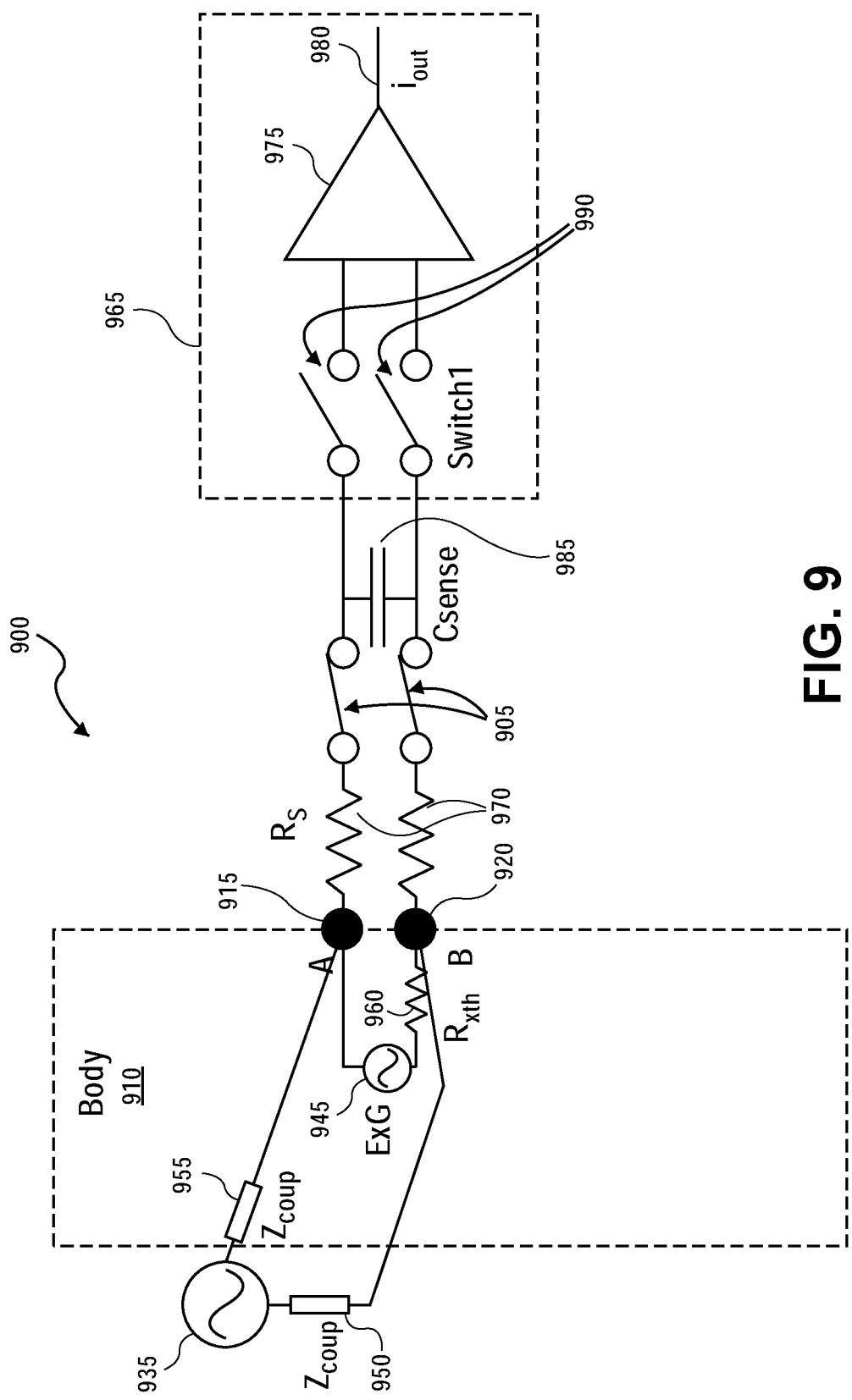
FIG. 9 is an exemplary schematic diagram of a biopotential measurement circuit comprising two sets of switches, in accordance with some embodiments of the disclosure provided herein.

FIG. 9 is an exemplary schematic diagram of a biopotential measurement circuit 900 comprising two sets of switches, 905, 990, in accordance with some embodiments of the disclosure provided herein. biopotential measurement system 900 comprises electromagnetic interference (EMI) voltage source 935, A lead coupled complex impedance 955, B lead coupled complex impedance 950, A lead electrode 915, B lead electrode 920, biopotential voltage source 945, biopotential Thevenin resistance 960, electrode resistances 970, sense capacitor 985, first switch 990, second switch 905 and current measurement 965.

According to some embodiments, electromagnetic interference (EMI) voltage source 935 models induced voltage on A and B lead electrodes 915, 920 from electromagnetic interference (EMI) passing through the air and body 910. Similarly, A lead coupled complex impedance 955 and B lead coupled complex impedance 950 model the complex coupled impedance from the electromagnetic interference (EMI) source and A lead electrode 915 and B lead electrode 920, passing through the ambient surrounds and body 910.

Similar to previous embodiments, biopotential voltage source 945 is a heuristic model of the biopotential of the heart. Similarly, biopotential Thevenin resistance 960 is the model Thevenin resistance associated with biopotential voltage source 945. Electrode resistances 970 are resistances associated with the sticky leads placed on the body 910. The use of another pair of switches 905 between Rs 970 and the sense capacitor 985 can be used to isolate the capacitor during measurement phase. The use of variable and programmable Rs/Csense to set the appropriate charging and discharge time. This method of measurement can be easily extended to many other fields.

For example, this system can be used in the measurement of chemical potentials such as pH. In this case, the amplifier attached to the electrode is expected to have high input impedance so as not to draw any current. In practice, a very small current always flows and thus any cell potential is capable of supplying a certain number of electrons. Thus, the circuits of FIGS. 9-10 can be used to measure the changes in the pH.

In this case B lead electrode 920 may be the reference electrode while A lead electrode 915 is connected to the solution to be measured. A very small current is drawn as the sense capacitor is charged after which the flow of the current automatically stops. The discharge of the capacitor as described above directly measures the cell potential and hence pH.

Figure 10:
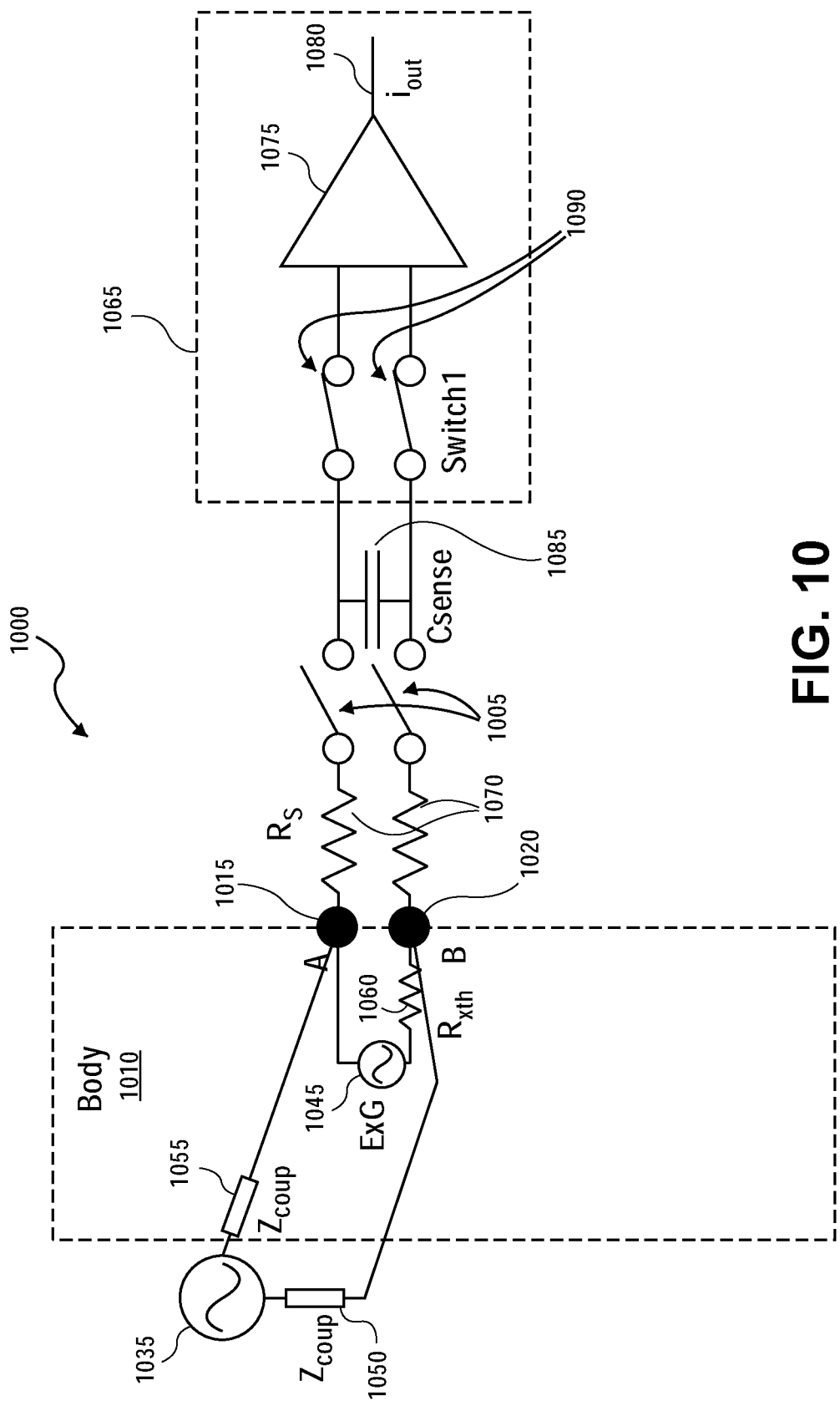
FIG. 10 is an exemplary schematic diagram of a biopotential measurement circuit comprising two sets of switches, in accordance with some embodiments of the disclosure provided herein.

FIG. 10 is an exemplary schematic diagram of a biopotential measurement circuit 1000 comprising two sets of switches, 1005, 1090, in accordance with some embodiments of the disclosure provided herein. biopotential measurement system 1000 comprises electromagnetic interference (EMI) voltage source 1035, A lead coupled complex impedance 1055, B lead coupled complex impedance 1050, A lead electrode 1015, B lead electrode 1020, biopotential voltage source 1045, biopotential Thevenin resistance 1060, electrode resistances 1070, sense capacitor 1085, first switch 1090, second switch 1005 and current measurement 1065.

In some embodiments, FIG. 9 can be considered the charging phase of the sense capacitor 1085. Conversely, FIG. 10 can be considered the measurement phase. FIG. 10 is included to complete the previous discussion relating to FIG. 9. That is, FIG. 10 represents the measuring phase where first set of switches 1090 is closed and the second set of switches 1005 are open. Whereas, FIG. 9 represent the charging phase where first set of switches 1090 is open and the second set of switches 1005 are closed.

Figure 11:
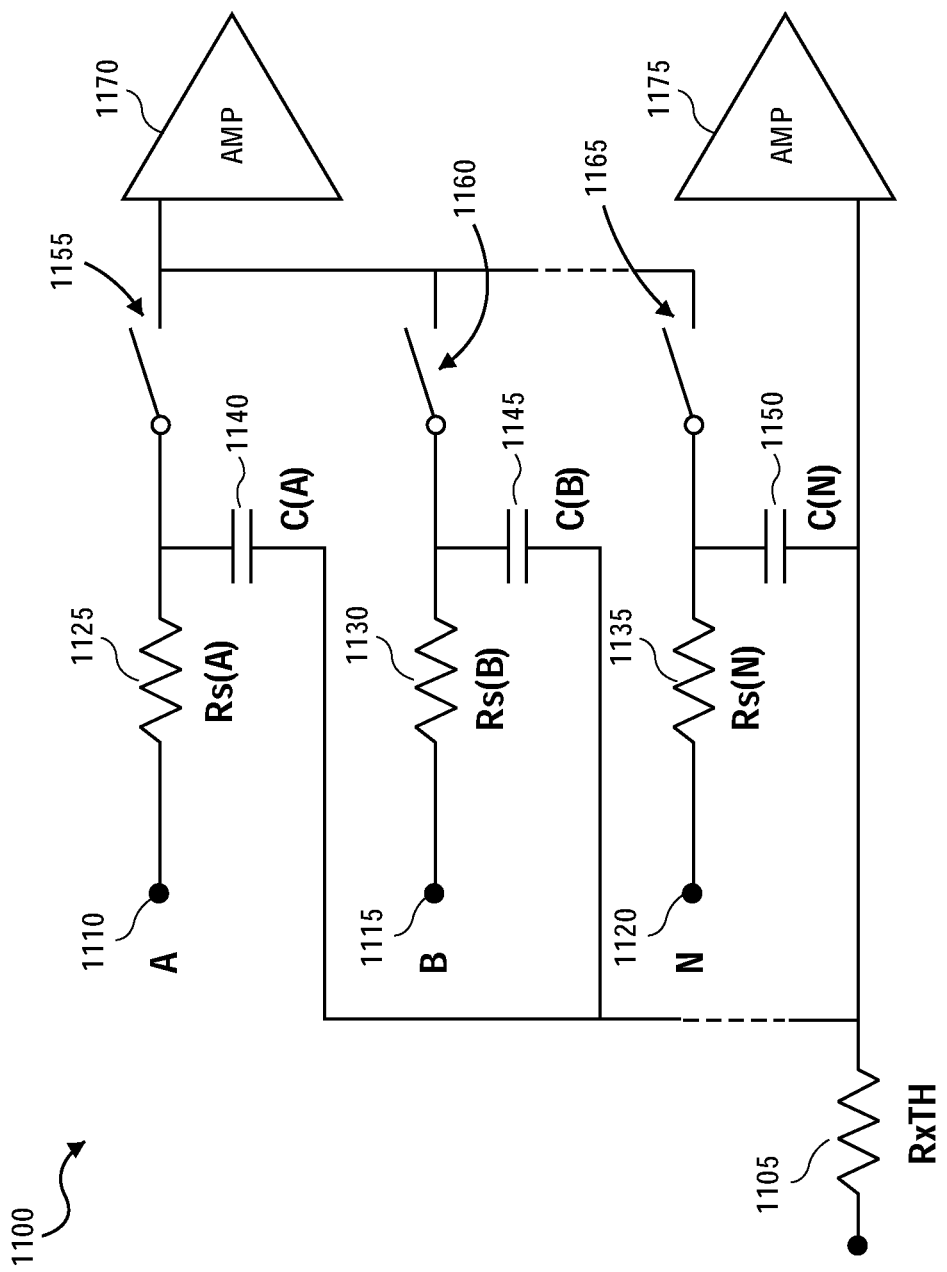
FIG. 11 is an exemplary schematic diagram of a biopotential measurement circuit that includes a plurality of measurement electrodes connected by switches, in accordance with some embodiments of the disclosure provided herein.

FIG. 11 is an exemplary schematic diagram of a biopotential measurement circuit 1100 that includes a plurality of measurement electrodes connected by switches, in accordance with some embodiments of the disclosure provided herein.

biopotential measurement system 1100 comprises A lead electrode 1110, B lead electrode 1115, biopotential, N lead electrode 1120, biopotential Thevenin resistance 1105, A electrode resistances Rs(A) 1125, B electrode resistances Rs(B) 1130, N electrode resistances Rs(N) 1135, A sense capacitor C(A) 1140, B sense capacitor C(B) 1145, N sense capacitor C(N) 1150, first switch 1155, second switch 1160, N switch 1165, current amplifier 1170 and current amplifier 1175. In some embodiments, amplifiers 1170, 1175 are the same amplifier. In other embodiments, they are a plurality as shown in FIG. 11.

In one or more embodiments, FIG. 11 exemplifies a schematic diagram of multiple ExG electrodes (A electrode resistances Rs(A) 1125, B electrode resistances Rs(B) 1130, N electrode resistances Rs(N) 1135) using a single amplifier 1170 and a multiplexer. In some embodiments, switches (first switch 1155, second switch 1160, N switch 1165) are temporally controlling in sequence by a switch controller (not pictured). In other embodiments, switches (first switch 1155, second switch 1160, N switch 1165) are implemented using a multiplexer with an input selected pin connected to a timing signal. The timing signal is based on the RC time constant of the electrode resistances and sense capacitance. Specifically, the period of the timing signal should be on the order of 3 RC time constants or more, in a preferred embodiment.

Since each electrode can charge its own sense capacitor (A sense capacitor C(A) 1140, B sense capacitor C(B) 1145, N sense capacitor C(N)), a single amplifier 1170 can serially read the charges from each of them by serially connecting to each of the capacitors (A sense capacitor C(A) 1140, B sense capacitor C(B) 1145, N sense capacitor C(N)) sequentially and reading them. Thus, a single amplifier may read tens to 100's of channels.

In some embodiments, this may be used for EEG or multi-electrode cardiography. However, the same amplifiers are easily configured to read photocurrents, in other embodiments. Thus, sequential use of the current measuring amplifier in which optical photocurrents are read in conjunction with biopotentials.

Figure 12:
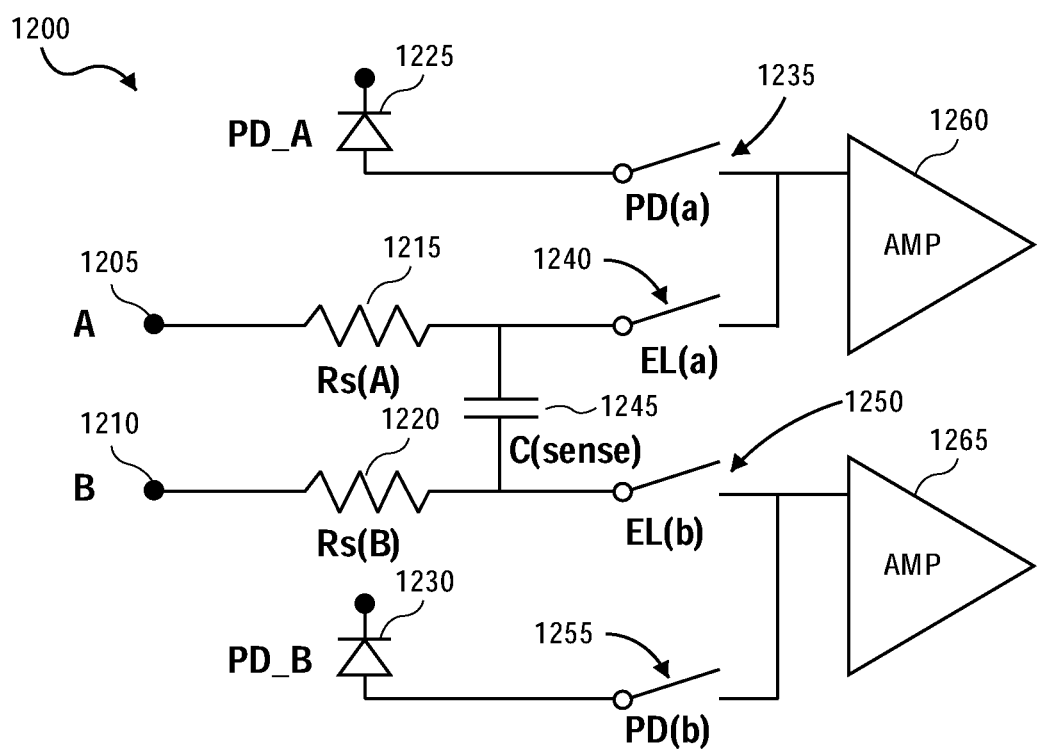
FIG. 12 is an exemplary schematic diagram of a biopotential measurement circuit configured to take electrical and optical measurements, in accordance with some embodiments of the disclosure provided herein.

Turning to FIG. 12, an exemplary schematic diagram of a biopotential measurement circuit 1200 is configured to take electrical and optical measurements, in accordance with some embodiments of the disclosure provided herein.

Biopotential measurement system 1200 comprises A lead electrode 1205, B lead electrode 1205, biopotential, A electrode resistances Rs(A) 1215, B electrode resistances Rs(B) 1220, sense capacitor C(sense) 1245, A PD 1225, B PD 1230, PD(a) switch 1235, EL(a) switch 1240, EL(b) 1250, PD(b) switch 1265, amplifier 1260 and amplifier 1265.

In practice, PD(a) switch 1235 and EL(a) switch 1240 are alternately switched on and off, each of which read by amp 1260. In a first cycle, sense capacitor 1245 is charged up from current derived from A node 1205, whereby PD(a) switch 1235 is open and EL(a) switch 1240 is closed. In a second cycle, sense capacitor 1245 is discharged through A PD 1225 as a function of light incident upon A PD 1225. In the second cycle, PD(a) switch 1235 is closed and EL(a) switch 1240 is open.

Similarly, PD(b) switch 1255 and EL(b) switch 1250 are alternately switched on and off, each of which read by amp 1265. In a first cycle, sense capacitor 1245 is charged up from current derived from B node 1210, whereby PD(b) switch 1250 is open and EL(a) switch 1255 is closed. In a second cycle, sense capacitor 1245 is discharged through B PD 1230 as a function of light incident upon A PD 1230. In the second cycle, PD(b) switch 1255 is closed and EL(b) switch 1250 is open.

Figure 13:
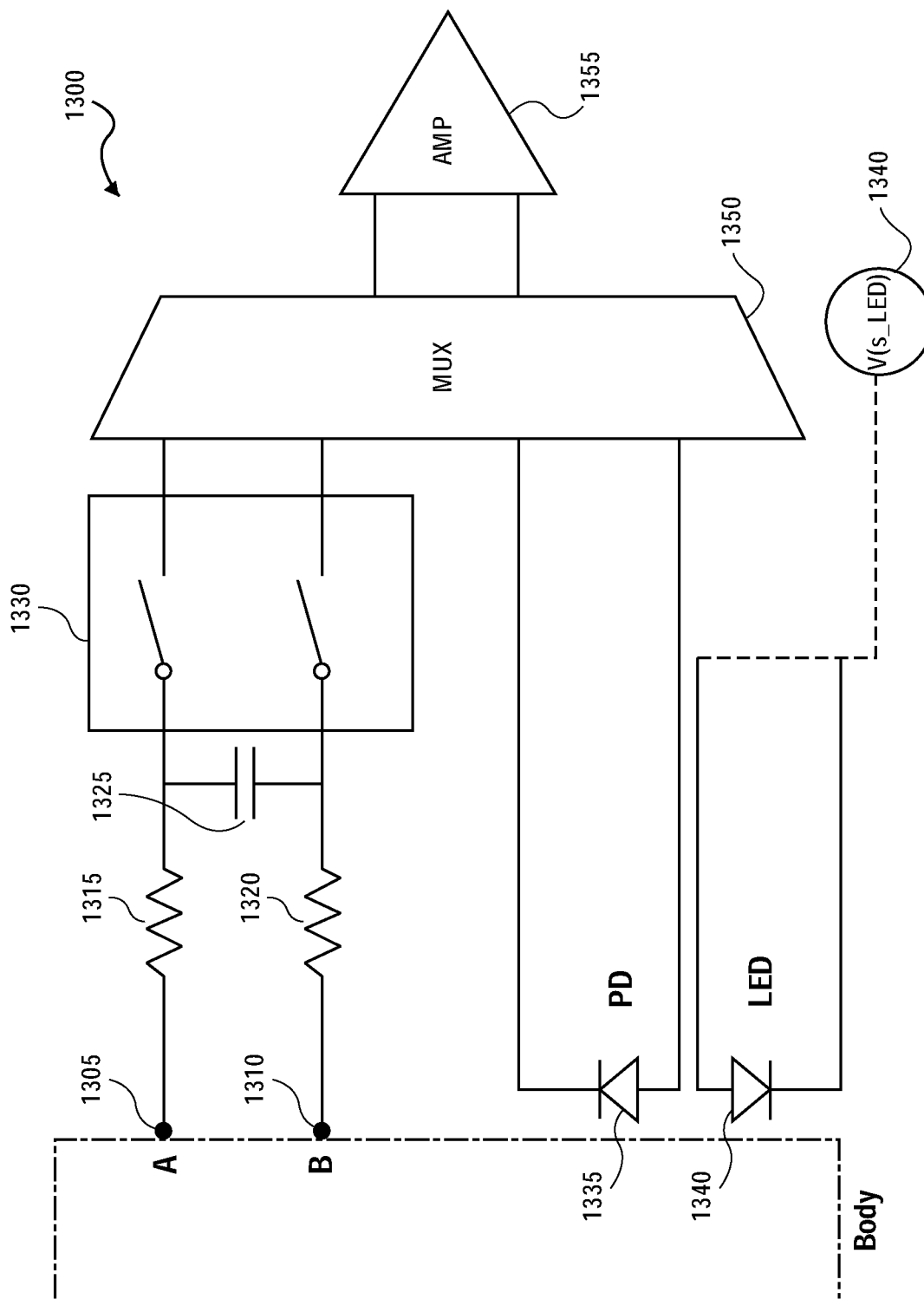
FIG. 13 is an exemplary schematic diagram of an example measurement circuit configured to take PPG and ECG measurements, in accordance with some embodiments of the disclosure provided herein.

FIG. 13 is an exemplary schematic diagram of an example measurement circuit 1300 configured to take plethysmograph (PPG) and electrocardiogram (ECG or EKG) measurements, in accordance with some embodiments of the disclosure provided herein. In some embodiments of making measurements, FIG. 13 illustrates a measurement circuit 1300 for measuring ExG and plethysmograph (PPG) using an optical element 1335 using a single amplifier 1355. This is useful in estimation of blood pressure which is often derived from observed timing differences of the two measurements.

A multiplexer 1350 inside the analog front end (AFE) switches alternately between electrocardiogram (ECG or EKG) and plethysmograph (PPG) connections. The electrocardiogram (ECG or EKG) measuring capacitor 1325 integrates the current from the body (nodes 1305, 1310) through electrode resistances 1315, 1320 and samples the electrocardiogram (ECG or EKG) when switch set 1330 is in the open position. This is passive measurement and requires no connection to the amplifier.

During this sampling, amp 1355 is connected to the optical element 1335 through multiplexer 1350 which measures the light transmitted through the tissue by blinking light source 1350. In one embodiment, optical element 1335 is a PD. However, other light detectors are not beyond the scope of the present disclosure. In some embodiments, light source 1350 is a LED. Yet, light source can be any suitable light source, such as, a broadband lamp with or without filtering, as is known in the art. Voltage source 1340 forward biases light source 1340, as in the case of a LED.

Once this sequence of measurements is complete, multiplexer 1350 is switched to the electrocardiogram (ECG or EKG) inputs, switch set 1330 is closed to read-out the charge accumulated on the capacitor 1325 which can occur fairly quickly (easily <20 us). As soon as the electrocardiogram (ECG or EKG) is read-out, plethysmograph (PPG) can be read while electrocardiogram (ECG or EKG) is sampled passively on the capacitor 1325. This cycle can repeat as often and at user determined rates.

Figure 14:
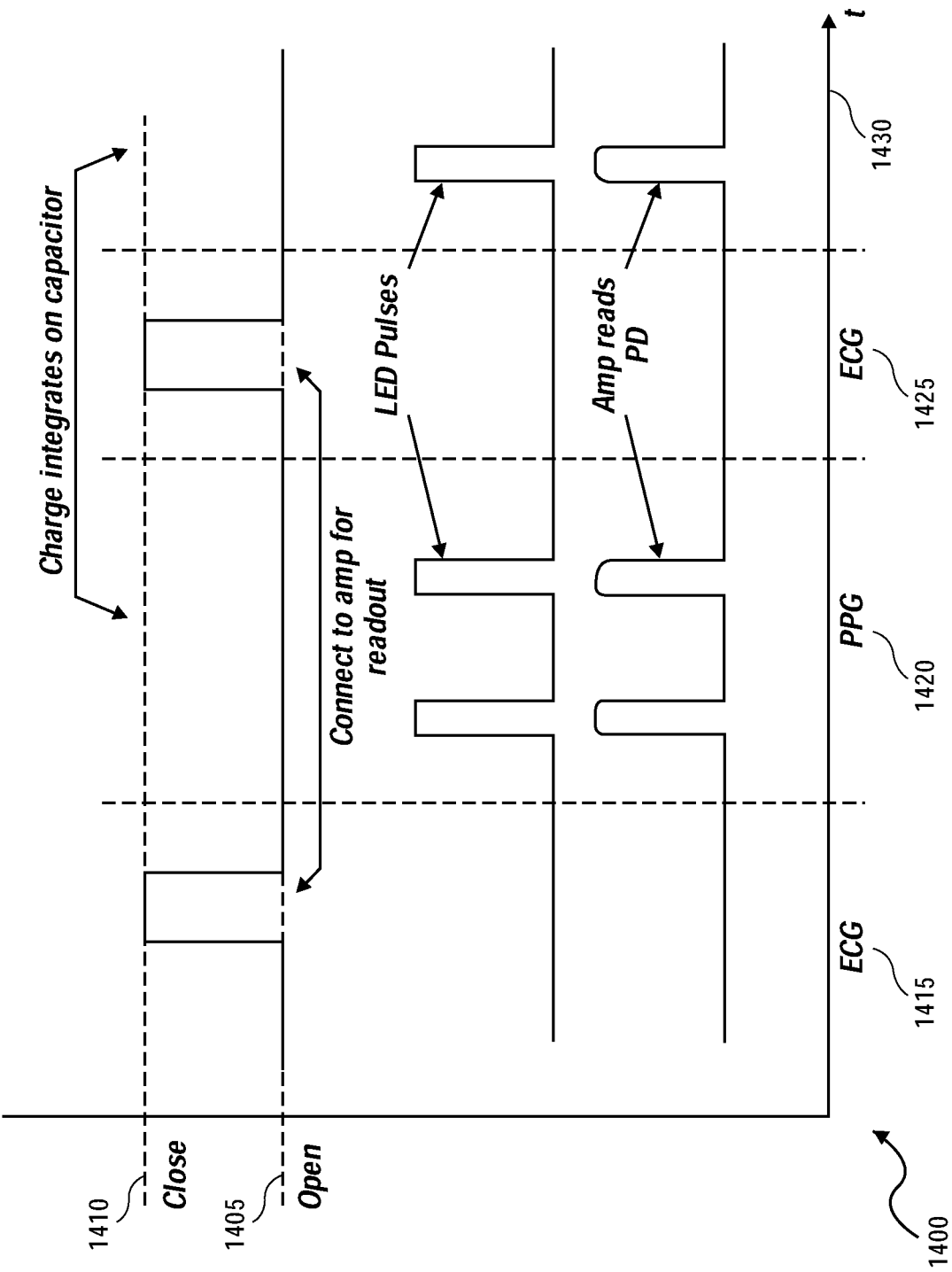
FIG. 14 illustrates an exemplary timing for controlling the plethysmograph (PPG) and ECG measurements, in accordance with some embodiments of the disclosure provided herein; and, FIG. 15 illustrates an exemplary apparatus for PPG and ECG measurements, in accordance with some embodiments of the disclosure provided herein.

Furthermore, this can be extended to measuring multiple electrocardiogram (ECG or EKG) and multiple photodiodes either as interleaved system of measurements as shown in the diagram of FIG. 14 or as sequential system of measurements.

FIG. 14 illustrates an exemplary timing for controlling the plethysmograph (PPG) and electrocardiogram (ECG or EKG) measurements 1400, in accordance with some embodiments of the disclosure provided herein. The electrocardiogram (ECG or EKG) sampling time 1420, 1430 on the capacitor T1 (when SW1 is open 1405) to electrocardiogram (ECG or EKG) measurement time T2 1415, 1425 (when SW1 is closed 1405 to read-out on the amplifier) have large ratio with typical numbers for T1 ranging from 50-1000 μs and T2 ranging from 2-10 μs. Thus, multiple measurements can be performed by the same amplifier during T1 phase by using the multiplexer to connect to different inputs which may be optical or electrical or even other electrocardiogram (ECG or EKG) channels.

Figure 15:
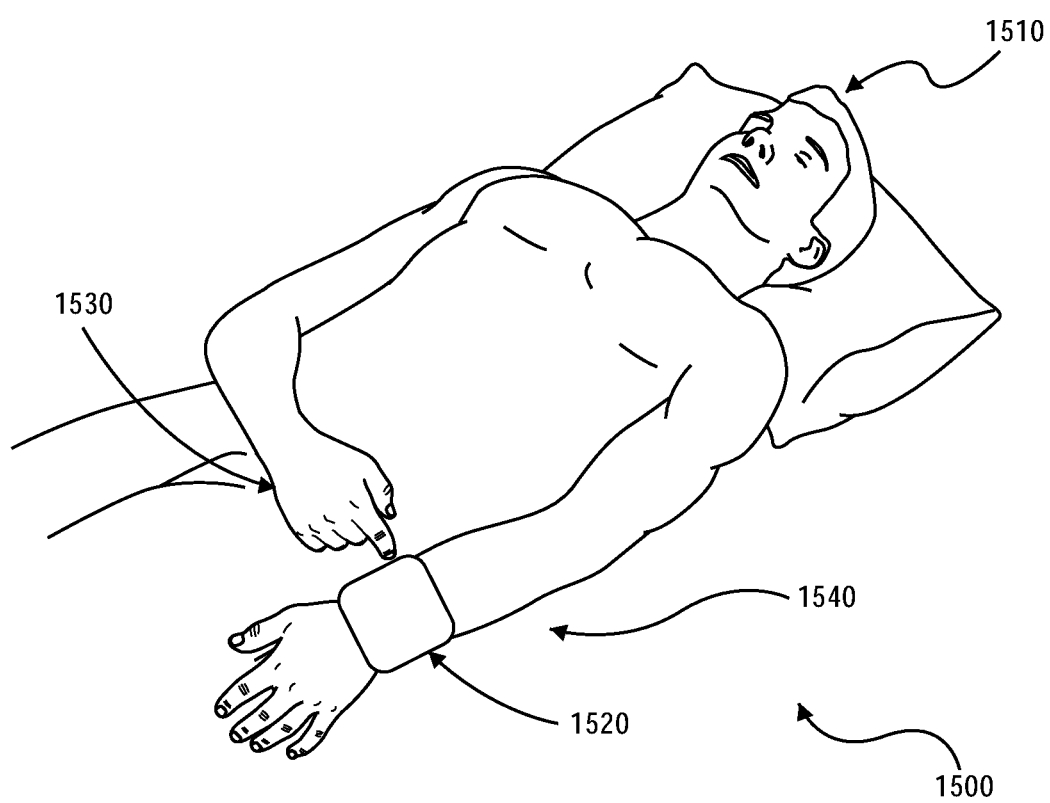

FIG. 15 illustrates an exemplary apparatus for plethysmograph (PPG) and electrocardiogram (ECG or EKG) measurements 1500, in accordance with some embodiments of the disclosure provided herein. In one embodiment, a wearable PPG/ECG device 1520 is disclosed. Wearable PPG/ECG device 1520 is implemented based on the previous discussion and embodiments, at least in part, using a single analog front end (AFE).

In practice, user 1510 creates a biopotential using arm 1530 opposite of arm 1540 whereon the wearable PPG/ECG device 1520 is disposed. Wearable PPG/ECG device 1520 also includes PPG measuring device. This is disclosed in greater detail in application Ser. No. 14/500,129 entitled, "LOW FREQUENCY NOISE IMPROVEMENT IN PLETHYSMOGRAPHY MEASUREMENT SYSTEMS," which hereby incorporated by reference in its entirety. In some embodiments, apparatus for plethysmograph (PPG) and ECG measurements 1500 is used to determine the phase velocity of arterial blood waves.

Pulse wave velocity (PWV) is the velocity at which the arterial pulse propagates through the circulatory system. PWV is used clinically as a measure of arterial stiffness. It is easy to measure invasively and non-invasively in humans, is highly reproducible, has a strong correlation with cardiovascular events and all-cause mortality and an indicator of target organ damage and a useful additional test in the investigation of hypertension. Additionally, high pulse wave velocity (PWV) has also been associated with poor lung function.

Having thus described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein.

Those skilled in the art will recognize or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments may be implemented in any of numerous ways. One or more aspects and embodiments of the present application involving the performance of processes or methods may utilize program instructions executable by a device (e.g., a computer, a processor, or other device) to perform, or control performance of, the processes or methods.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above.

The computer readable medium or media may be transportable, such that the program or programs stored thereon may be loaded onto one or more different computers or other processors to implement various ones of the aspects described above. In some embodiments, computer readable media may be non-transitory media.

The terms "program" or "software" are used herein in a generic sense to refer to any type of computer code or set of computer-executable instructions that may be employed to program a computer or other processor to implement various aspects as described above. Additionally, it should be appreciated that according to one aspect, one or more computer programs that when executed perform methods of the present application need not reside on a single computer or processor but may be distributed in a modular fashion among a number of different computers or processors to implement various aspects of the present application.

Computer-executable instructions may be in many forms, such as program modules, executed by one or more computers or other devices. Generally, program modules include routines, programs, objects, components, data structures, etc. that performs particular tasks or implement particular abstract data types. Typically, the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

When implemented in software, the software code may be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a personal digital assistant (PDA), a smart phone, a mobile phone, an iPad, or any other suitable portable or fixed electronic device.

Also, a computer may have one or more input and output devices. These devices can be used, among other things, to present a user interface. Examples of output devices that may be used to provide a user interface include printers or display screens for visual presentation of output and speakers or other sound generating devices for audible presentation of output. Examples of input devices that may be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks or wired networks.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined.

Elements other than those specifically identified by the "and/or" clause may optionally be present, whether related or unrelated to those elements specifically identified. Thus, as a non-limiting example, a reference to "A and/or B", when used in conjunction with open-ended language such as "comprising" may refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, the term "between" is to be inclusive unless indicated otherwise. For example, "between A and B" includes A and B unless indicated otherwise.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

The present invention should therefore not be considered limited to the particular embodiments described above. Various modifications, equivalent processes, as well as numerous structures to which the present invention may be applicable, will be readily apparent to those skilled in the art to which the present invention is directed upon review of the present disclosure.

The present invention should therefore not be considered limited to the particular embodiments described above. Various modifications, equivalent processes, as well as numerous structures to which the present invention may be applicable, will be readily apparent to those skilled in the art to which the present invention is directed upon review of the present disclosure.

What is claimed is:

1. An apparatus for measuring lead-off detection and biopotential of a patient comprising:
    a first lead electrode electrically connected in series to a first high resistance passive resistor at a proximal end of the first high resistance passive resistor, the first lead electrode configured to make direct electrical contact with the patient's skin;
    a second lead electrode electrically connected in series to a second high resistance passive resistor at a proximal end of the second high resistance passive resistor, the second lead electrode configured to make direct electrical contact with the patient's skin;
    a first and second switch in electrical communications with the distal ends of the first and second high resistance passive resistors, respectively;
    a capacitor electrically connected in parallel between the distal ends of the first and second high resistance passive resistors and the first and second switches; and
    a differential amplifier whose inputs are derived from the first and second switches;
    wherein, the switches are configured to open and close so as to charge and discharge the capacitor, respectively after a predetermined time constant period and the electrical pathways from the first and second lead electrodes to the amplifier are DC coupled.

2. The apparatus of claim 1, wherein the predetermined time constant period is based on an RC time constant which is determined by at least two of: the first high resistance passive resistor, the second high resistance passive resistor, and the capacitor.

3. The apparatus of claim 2, wherein the predetermined time constant period is long enough to allow the capacitor to charge to potential substantially close to that of the patient's bio-potential.

4. The apparatus of claim 3, wherein the predetermined time constant period is at least three RC time constant.

5. The apparatus of claim 1, wherein the differential amplifier is a current amplifier.

6. The apparatus of claim 5 wherein the current amplifier has 100 fA of RMS noise in 100 Hz bandwidth.

7. The apparatus of claim 1, wherein the differential amplifier is an integrating amplifier.

8. The apparatus of claim 7, whereby the integrating amplifier supplies an output which is proportional to current integrated over a fixed amount of time and proportional to an accumulated charge.

9. The apparatus of claim 1, further comprising a current sensor in electrical communication with a differential amplifier output.

10. The apparatus of claim 9, wherein the differential amplifier output current is restricted to a small value by a large series resistor (Rs).

11. The apparatus of claim 9, wherein the current sensor is a hall effect sensor.

12. The apparatus of claim 9, wherein the current sensor is an ammeter.

13. The apparatus of claim 9, wherein the current sensor is configured to measure an electromagnetic field proximal to the output of the differential amplifier.

14. The apparatus of claim 1, wherein at least one of the first resistance passive resistor and second high resistance passive resistor is greater than 100 kΩ.

15. The apparatus of claim 1, wherein the apparatus is a wearable device.

16. The apparatus of claim 1 further comprising a third and fourth switch in electrical communications with the first and second switches, respectively.

17. A method for measuring lead-off detection and biopotential of a patient comprising:
    providing a first lead electrode and second lead electrode, the first and second lead electrodes configured to make direct electrical contact with the patient's skin;
    electrically connecting a proximal end of a first high resistance resistor to the first lead electrode;
    electrically connecting a proximal end of a second high resistance resistor to the second lead electrode;
    disposing a first and second switch between the distal ends of the first and second high resistance resistors, respectively and a current amplifier;

switching the first and second switches to a closed position;

DC coupling both electrical pathways from the first and second lead electrodes to the amplifier;

measuring the current from the output of the current amplifier; and calculating a patient's biopotential at least based on a measured output of the current amplifier.

18. The method of claim 17, further comprising measuring an average current in a given time interval by charging a capacitor disposed between the distal ends of the first and second high resistance resistors.

19. The method of claim 18, further comprising measuring electrode impedance by measuring currents through the amplifier which is used for measuring biopotential generated currents.

20. A system for measuring lead-off detection and biopotential of a patient comprising:

means for providing a first lead electrode and second lead electrode, the first and second lead electrodes configured to make direct electrical contact with the patient's skin;

a circuit comprising:

first means for resisting current and in electrical communication with the first lead electrode;

second means for resisting current and in electrical communication with the second lead electrode;

means for storing charge from the first and second means for resisting current;

means for amplifying the current from the means for storing charge;

means for switching current on and off between the distal ends of the first and second means for resisting current and means for amplifying the current;

means for measuring the current from the output of the means for amplifying; and means for calculating a patient's biopotential at least based on the measured output of the means for amplifying.

* * * * *